(12) United States Patent
Srinivasan et al.

(10) Patent No.: US 11,279,696 B2
(45) Date of Patent: Mar. 22, 2022

(54) PROCESSES FOR THE PREPARATION OF 7-{4-[4-(1-BENZOTHIOPHEN-4-YL) PIPERAZIN-1-YL]BUTOXY}QUINOLIN-2 (1H)-ONE

(71) Applicant: MSN LABORATORIES PRIVATE LIMITED, Telangana (IN)

(72) Inventors: Thirumalai Rajan Srinivasan, Hyderabad (IN); Eswaraiah Sajja, Hyderabad (IN); Venkat Reddy Ghojala, Hyderabad (IN); Rajashekar Kommera, Hyderabad (IN)

(73) Assignee: MSN LABORATORIES PRIVATE LIMITED, Telangana (IN)

( * ) Notice: Subject to any disclaimer, the term of this patent is extended or adjusted under 35 U.S.C. 154(b) by 365 days.

(21) Appl. No.: 16/348,791

(22) PCT Filed: Nov. 7, 2017

(86) PCT No.: PCT/IN2017/000128
§ 371 (c)(1),
(2) Date: May 9, 2019

(87) PCT Pub. No.: WO2018/087775
PCT Pub. Date: May 17, 2018

(65) Prior Publication Data
US 2019/0359606 A1    Nov. 28, 2019

(30) Foreign Application Priority Data

Nov. 9, 2016  (IN) .............................. 201641038235
Mar. 30, 2017  (IN) .............................. 201741011361

(51) Int. Cl.
*C07D 409/12*    (2006.01)

(52) U.S. Cl.
CPC ........ *C07D 409/12* (2013.01); *C07B 2200/13* (2013.01)

(58) Field of Classification Search
CPC .................................................... C07D 409/12
See application file for complete search history.

(56) References Cited

FOREIGN PATENT DOCUMENTS

WO    WO2006112464    10/2006

OTHER PUBLICATIONS (ISA/210) International Search Report mailed by the Patent Cooperation Treaty dated Jan. 18, 2018.
(ISA/237) Written Opinion of the International Searching Authority mailed by the Patent Cooperation Treaty dated Jan. 18, 2018.

*Primary Examiner* — Patricia L Morris
(74) *Attorney, Agent, or Firm* — IP Pundit LLC

(57) ABSTRACT

The Present Invention relates to process for the preparation of 7-{4-[4-(1-benzothiophen-4-yl)piperazin-1-yl] butoxy}quinolin-2(1H)-one represented by the following structural formula-1.

Formula-1

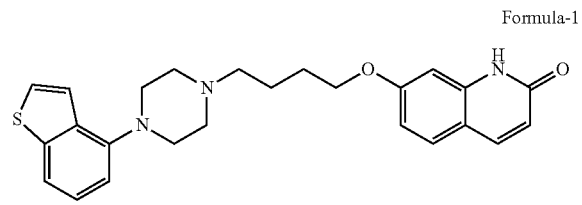

4 Claims, 3 Drawing Sheets

PROCESSES FOR THE PREPARATION OF 7-{4-[4-(1-BENZOTHIOPHEN-4-YL) PIPERAZIN-1-YL]BUTOXY}QUINOLIN-2(1H)-ONE

RELATED APPLICATIONS

This application claims the benefit of priority of our Indian patent applications 201641038235 filed on Nov. 9, 2016 and 201741011361 filed on Mar. 30, 2017 both of which are incorporated herein as reference.

FIELD OF THE INVENTION

The present invention provides various processes for the preparation of 7-{4-[4-(1-benzothiophen-4-yl)piperazin-1-yl]butoxy}quinolin-2(1H)-one represented by the following structural formula-1.

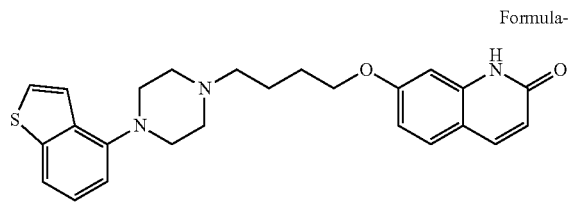

Formula-1

The present invention also provides processes for the preparation of crystalline compound of formula-1.

BACKGROUND OF THE INVENTION

7-{4-[4-(1-benzothiophen-4-yl)piperazin-1-yl]butoxy}quinolin-2(1H)-one (also known as Brexpiprazole, and previously known as OPC-34712) is a novel atypical antipsychotic drug. It is a D2 dopamine partial agonist called serotonin-dopamine activity modulator (SDAM). The drug received USFDA approval on Jul. 10, 2015 for the treatment of schizophrenia, and as an adjunctive treatment for depression and is marketed under the brand name REXULTI®.

U.S. Pat. No. 7,888,362B2 (herein after referred as US'362 patent) described 7-{4-[4-(1-benzothiophen-4-yl)piperazin-1-yl]butoxy}quinolin-2(1H)-one, its pharmaceutically acceptable salts and processes for their preparation.

The process described in US'362 patent has several disadvantages to adopt it on commercial scale. The said process involves column chromatography technique at every stage of the synthetic process to purify the products. Column chromatography is a cumbersome, costly and time taking process and hence its use is not viable on commercial scale.

Hence, there is always a significant need in the art to develop a simple, safe, ecofriendly and commercially viable process for the preparation of 7-{4-[4-(1-benzothiophen-4-yl)piperazin-1-yl]butoxy}quinolin-2(1H)-one which provides the product with good yield and quality.

Brexpiprazole and its hydrochloride salt can exist in different polymorphic forms which may differ from each other in terms of stability, physical properties, spectral data and methods of preparation. However, there is still a need for novel crystalline forms, which are more stable, reproducible and free of other polymorphic forms.

WO 2006/112464 A1 discloses brexpiprazole and its use for the treatment of schizophrenia and other central nervous system disorders. Brexpiprazole is described in example 1 as a crystalline material obtained as a white powder by recrystallization from ethanol.

WO 2013/162046 A1 characterizes the crystalline brexpiprazole obtained from example 1 of WO 2006/112464 A1 as an "anhydride", more properly to be understood as an "anhydrate" form of brexpiprazole. Brexpiprazole anhydrate, herein referred to as form-I, shows characteristic PXRD reflections at 2 Theta angles of 14.4°, 19.1°, 20.2°, 21.3° and 23.2°.

WO 2013/162046 A1 also discloses a crystalline hydrate and crystalline dihydrate of brexpiprazole which is characterized by means of PXRD. Brexpiprazole hydrate is described as showing characteristic PXRD reflections at 2 Theta angles of 7.7°, 9.4°, 11.8°, 18.9° and 24.0°. Brexpiprazole dihydrate is described as showing characteristic PXRD reflections at 2 Theta angles of 8.1°, 8.9°, 15.1°, 15.6° and 24.4°.

CN 104844586 A discloses Brexpiprazole amorphous form and its process for the preparation thereof.

CN 104829603 A discloses Brexpiprazole hydrochloride monohydrate and process for the preparation.

RD617033 discloses the PXRD pattern of Brexpiprazole HCl salt obtained according to the process exemplified in U.S. Pat. No. 9,499,525B2 herein referred to as form-I.

The PXRD pattern of crystalline form-I of MSNL produced 7-{4-[4-(1-benzothiophen-4-yl)piperazin-1-yl]butoxy}quinolin-2(1H)-one hydrochloride is similar to PXRD pattern of crystalline form-I of 7-{4-[4-(1-benzothiophen-4-yl)piperazin-1-yl]butoxy}quinolin-2(1H)-one hydrochloride disclosed in RD617033.

The present invention provides various processes for the preparation and purification of 7-{4-[4-(1-benzothiophen-4-yl)piperazin-1-yl]butoxy}quinolin-2(1H)-one and its intermediate compounds and polymorph processes.

The process for the preparation of compound of formula-1 of present invention provides simple, safe, ecofriendly and commercially viable process by using simple and commercially available raw materials, reagents & solvents.

The present invention also provides various processes for the preparation of 7-{4-[4-(1-benzothiophen-4-yl)piperazin-1-yl]butoxy}quinolin-2(1H)-one hydrochloride salt and it's novel polymorphs, which can be used as an intermediate in the preparation of Brexpiprazole.

BRIEF DESCRIPTION OF THE INVENTION

The first aspect of the present invention is to provide a process for the preparation of 7-{4-[4-(1-benzothiophen-4-yl)piperazin-1-yl]butoxy}quinolin-2(1H)-one compound of formula-1.

The second aspect of the present invention is to provide a process for the preparation of 7-hydroxyquinolin-2(1H)-one compound of formula-3, comprising of oxidizing the 7-hydroxy-3,4-dihydroquinolin-2(1H)-one compound of formula-2 with a suitable oxidizing agent in a suitable solvent to provide compound of formula-3.

The third aspect of the present invention is to provide an improved process for the preparation of compound of formula-1.

The fourth aspect of the present invention is to provide a process for the purification of compound of formula-1.

The fifth aspect of the present invention is to provide a process for the preparation of crystalline form-I of 7-{4-[4-(1-benzothiophen-4-yl)piperazin-1-yl]butoxy}quinolin-2(1H)-one hydrochloride compound of formula-1a.

The sixth aspect of the present invention is to provide a process for the purification of compound of formula-1a.

The seventh aspect of the present invention is to provide another process for the purification of compound of formula-1a.

The eighth aspect of the present invention is to provide a process for the preparation of compound of formula-1.

The ninth aspect of the present invention is to provide a process for the preparation of crystalline compound of formula-1.

The tenth aspect of the present invention is to provide alternate process for the preparation of crystalline compound of formula-1.

The eleventh aspect of the present invention is to provide novel crystalline polymorph of 7-{4-[4-(1-benzothiophen-4-yl)piperazin-1-yl]butoxy}quinolin-2(1H)-one hydrochloride compound of formula-1a, herein after designated as form-II.

The twelfth aspect of the present invention is to provide a process for the preparation of crystalline form-II of compound of formula-1a.

The thirteenth aspect of the present invention is to provide novel crystalline polymorph of compound of formula-1a, herein after designated as form-III.

The fourteenth aspect of the present invention is to provide a process for the preparation of crystalline form-III of compound of formula-1a.

The fifteenth aspect of the present invention is to provide a process for the preparation of 7-{4-[4-(1-benzothiophen-4-yl)piperazin-1-yl]butoxy}quinolin-2(1H)-one compound of formula-1.

The sixteenth aspect of the present invention is to provide another process for the preparation of compound of formula-1.

The seventeenth aspect of the present invention is to provide alternative process for the preparation of compound of formula-1.

The eighteenth aspect of the present invention is to provide another process for the preparation of compound of formula-1.

The nineteenth aspect of the present invention is to provide alternative process for the preparation of compound of formula-1.

BRIEF DESCRIPTION OF THE DRAWINGS

FIG. 1: Illustrates the PXRD pattern of compound of formula-4a.

FIG. 2: Illustrates the PXRD pattern of compound of formula-6a.

FIG. 4: Illustrates the PXRD pattern of crystalline form-I of compound of formula-1a.

FIG. 5: Illustrates the PXRD pattern of crystalline form-II of compound of formula-1a.

FIG. 6: Illustrates the PXRD pattern of crystalline form-III of compound of formula-1a.

DETAILED DESCRIPTION OF THE INVENTION

Figure 1:
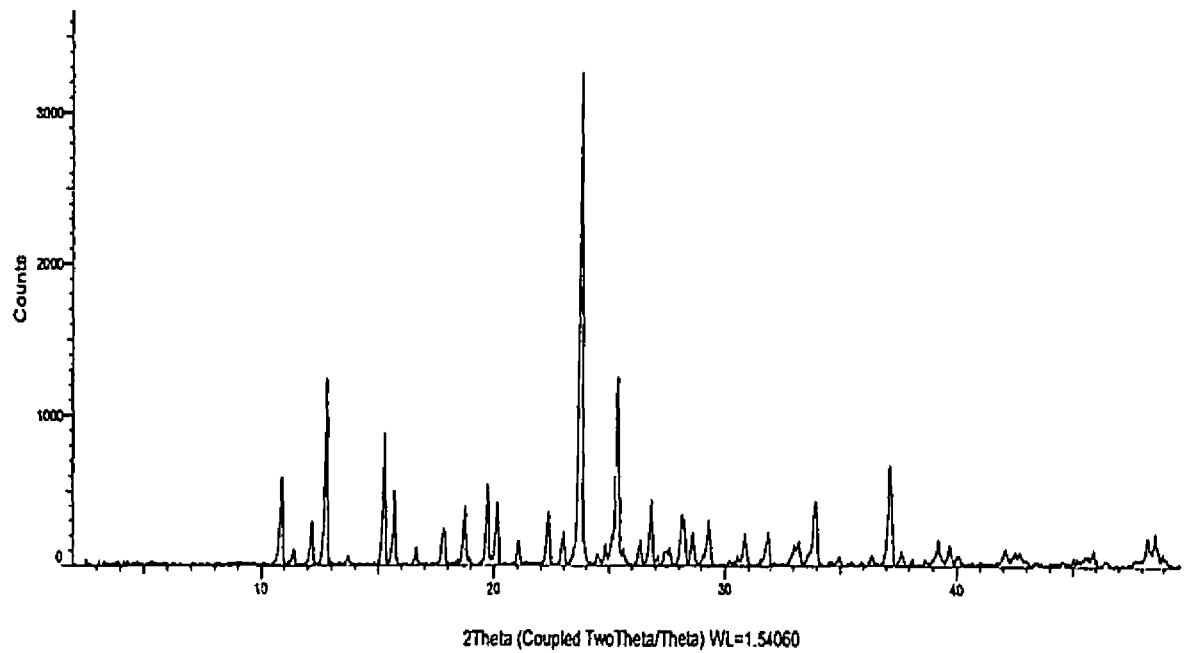

The "suitable solvent" used in the present invention can be selected from but not limited to "hydrocarbon solvents" such as n-pentane, n-hexane, n-heptane, cyclohexane, pet ether, benzene, toluene, xylene and the like; "ether solvents" such as dimethyl ether, diethyl ether, diisopropyl ether, methyl tert-butyl ether, 1,2-dimethoxyethane, tetrahydrofuran, 1,4-dioxane and the like; "ester solvents" such as methyl acetate, ethyl acetate, n-propyl acetate, isopropyl acetate, n-butyl acetate, isobutyl acetate, tert-butyl acetate and the like; "polar-aprotic solvents" such as dimethylacetamide, dimethylformamide, dimethylsulfoxide, N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutyl ketone and the like; "nitrile solvents" such as acetonitrile, propionitrile, isobutyronitrile and the like; "alcohol solvents" such as methanol, ethanol, n-propanol, iso-propanol, n-butanol, iso-butanol, 2-butanol, tert-butanol, ethane-1,2-diol, propane-1,2-diol and the like; "polar solvents" such as water; formic acid, acetic acid and the like or mixture of any of the afore mentioned solvents.

The "suitable base" used in the present invention can be selected from but not limited to "inorganic bases" selected from "alkali metal carbonates" such as sodium carbonate, potassium carbonate, lithium carbonate; cesium carbonate and the like; "alkali metal bicarbonates" such as sodium bicarbonate, potassium bicarbonate, lithium bicarbonate, cesium bicarbonate and the like; "alkali metal hydroxides" such as sodium hydroxide, potassium hydroxide, lithium hydroxide, cesium hydroxide and the like; "alkali metal alkoxides" such as sodium methoxide, sodium ethoxide, potassium methoxide, potassium ethoxide, lithium methoxide, lithium ethoxide, sodium tert.butoxide, potassium tert-.butoxide, lithium tert.butoxide and the like; "alkali metal hydrides" such as sodium hydride, potassium hydride, lithium hydride and the like; "alkali metal amides" such as sodium amide, potassium amide, lithium amide and the like; alkali metal and alkali earth metal salts of acetic acid such as sodium acetate, potassium acetate, magnesium acetate, calcium acetate and the like; ammonia; "organic bases" like dimethylamine, diethylamine, diisopropyl mine, diisopropylethylamine (DIPEA), diisobutylamine, triethylamine, triisopropylamine, tributylamine, tert.butyl amine, pyridine, piperidine, 4-dimethylaminopyridine (DMAP), quinoline, imidazole, N-methylimidazole, 1,8-diazabicyclo[5.4.0]undec-7-ene (DBU), 1,5-diazabicyclo[4.3.0]non-5-ene (DBN), dimethylaniline, N-methylmorpholine (NMM), 1,4-diazabicyclo[2.2.2]octane (DABCO), 2,6-lutidine and the like; "organolithium bases" such as methyl lithium, n-butyl lithium, lithium diisopropylamide (LDA) and the like; "organosilicon bases" such as lithium hexamethyldisilazide (LiHMDS), sodium hexamethyldisilazide (NaHMDS), potassium hexamethyldisilazide (KHMDS) and the like or their mixtures.

The "suitable inorganic acid" used in the present invention can be selected from but not limited to hydrochloric acid, hydrobromic acid, sulfuric acid, phosphoric acid, nitric acid.

The "suitable oxidizing agent" used in the present invention can be selected from but not limited to 4,5-dichloro-3,6-dihydroxyphthalonitrile (DDQ), 2,3,5,6-tetrachlorocyclohexa-2,5-diene-1,4-dione (Chloranil), potassium permanganate ($KMnO_4$), m-chloroperbenzoic acid (MCPBA), hydrogen peroxide ($H_2O_2$), NBS-benzoyl peroxide, Zinc powder, Pd/C, Manganese dioxide, ceric ammonium nitrate (CAN), elemental sulfur, nitrobenzene and the like.

The "suitable alkali metal halide" can be selected from but not limited to NaCl, NaBr, NaI, KCl, KBr, KI, CsCl, CsBr, CsI and the like.

The "suitable halogenating agent" can be selected from but not limited to $Cl_2$, $Br_2$, $I_2$, HBr, $SOCl_2$, $PCl_3$, $PBr_3$, $PCl_5$, POCl₃, N-chlorosuccinimide (NCS), N-bromosuccinimide (NBS), N-iodosuccinimide (NIS) and the like.

The "suitable coupling agent" can be selected from but not limited to N,N'-dicyclohexylcarbodiimide (DCC), N,N'-diisopropylcarbodiimide (DIC), 1-ethyl-3-(3-dimethylaminopropyl)carbodiimide hydrochloride (EDC.HCl), N,N'-carbonyldiimidazole (CDI), 1-[bis(dimethylamino)methylene]-1H-1,2,3-triazolo[4,5-b]pyridinium 3-oxid hexafluorophosphate (HATU), 2-(1H-benzotriazol-1-yl)-1,1,3,3-tetramethyluronium hexafluorophosphate (HBTU), 1H-benzotriazolium 1-[bis(dimethylamino)methylene]-5chloro-hexafluorophosphate (1-) 3-oxide (HCTU), alkyl or aryl chloroformates such as methyl chloroformate, ethyl chloroformate, benzylchloroformate, diphenylphosphoroazidate (DPPA), thionyl chloride, oxalyl chloride, phosphorous oxychloride, phosphorous pentachloride, 4-methyl-2-oxopentanoyl chloride (i-BuCOCOCl), (benzotriazol-1-yloxy)tris(dimethylamino)phosphonium hexafluorophosphate (BOP), benzotriazol-1-yl-oxytripyrrolidinophosphonium hexafluorophosphate (PyBOP), methane sulfonyl chloride and the like optionally in combination with 1-hydroxy-7-azatriazole (HOAt), 1-hydroxybenzotriazole (HOBt), 1-hydroxy-1H-1,2,3-triazole-4-carboxylate (HOCt), O-(benzotriazol-1-yl)-N,N,N',N'-tetramethyluronium tetrafluoroborate (TBTU), N-hydroxysuccinamide (HOSu), N-hydroxysulfosuccinimide (Sulfo-NHS) and the like.

The suitable "amine protecting group" or "N-protecting group" 'P' can be selected from but not limited to alkoxycarbonyl such methoxycarbonyl (Moc), ethoxycarbonyl, tert-butyloxycarbonyl (Boc), benzyloxycarbonyl (Cbz), p-methoxybenzyl carbonyl (Moz or MeOZ), 9-fluorenylmethyloxy carbonyl (FMOC), acetyl (Ac), benzoyl (Bz), benzyl (Bn), carbamate group, p-methoxyphenyl (PMP), p-methoxybenzyl (PMB), 3,4-dimethoxybenzyl (DMPM), tosyl (Ts), trifluoroacetyl (TFA), trichloroethyl chloroformate (Troc), pivaloyl (Piv) group and the like.

The suitable amine protecting agent is selected such that it is capable of protecting the nitrogen atom with any of the above mentioned amine protecting groups.

Suitable amine protecting agent is selected from but not limited to di-tert.butyl dicarbonate (DIBOC), benzyl chloroformate, fluorenylmethyloxy carbonyl chloride (FMOC chloride), acetyl chloride, acetic anhydride, benzoyl halides, benzyl halides, alkyl haloformates such as methyl chloroformate, ethyl chloroformate, isopropyl chloroformate and the like, tosyl halides, tosyl anhydrides, alkyl trifluoroacetates such as methyl trifluoroacetate, ethyl trifluoroacetate, isopropyl trifluoroacetate, vinyl trifluoroacetate, trifluoroacetic acid, trifluoroacetyl chloride and the like.

The suitable deprotecting agent is selected based on the protecting group employed. The suitable deprotecting agent can be selected from but not limited to acids such as hydrochloric acid, hydrobromic acid, sulfuric acid, nitric acid, aq.phosphoric acid, trifluoroacetic acid, methane sulfonic acid, p-toluenesulfonic acid; acetyl chloride in combination with alcohols; bases such as alkali metal hydroxides, alkali metal carbonates, cesium carbonate/imidazole, alkali metal bicarbonates, ammonia, aqueous ammonia, ammonium cerium(IV) nitrate (CAN); and organic bases such as methylamine, ethylamine, diethylamine, triethylamine, piperidine; hydrogenating agents such as Pd/C, Pd(OH)₂/C (Pearlman's catalyst), palladium acetate, platinum oxide, platinum black, sodium borohydride, Na-liquid ammonia, Raney-Ni, Zn-acetic acid, tri($C_1$-$C_6$)alkylsilanes, tri($C_1$-$C_6$) alkylsilyl halides and the like.

In the present invention, the groups '$X_1$', '$X_2$' are same or different and can be independently selected from leaving groups such as halogen, substituted/unsubstituted alkyl/aryl sulfonyloxy.

'X' represents halogen such as F, Cl, Br and I; 'R' represents $C_1$-$C_6$ straight chain or branched chain alkyl groups.

The first aspect of the present invention provides a process for the preparation of 7-{4-[4-(1-benzothiophen-4-yl)piperazin-1-yl]butoxy}quinolin-2(1H)-one compound of formula-1, comprising of;

a) oxidizing the 7-hydroxy-3,4-dihydroquinolin-2(1H)-one compound of formula-2

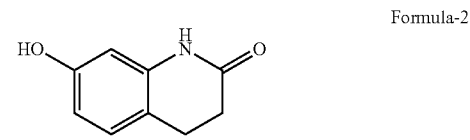 [SMILES: O=C1CCc2ccc(O)cc2N1]

Formula-2 with a suitable oxidizing agent in a suitable solvent to provide 7-hydroxyquinolin-2(1H)-one compound of formula-3,

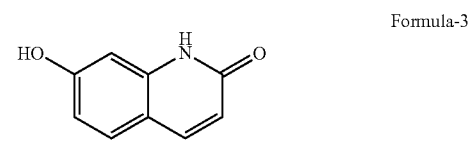 [SMILES: O=c1ccc2ccc(O)cc2[nH]1]

Formula-3 b) reacting the compound of formula-3 with 1,4-disubstituted butane having the following structural formula

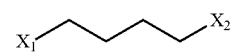

wherein, '$X_1$', '$X_2$' have the meaning as defined above; in presence of a suitable base in a suitable solvent to provide compound of general formula-4,

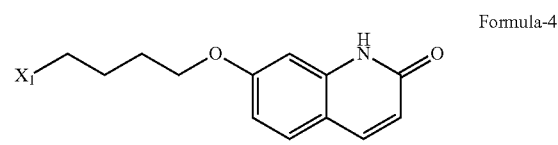

Formula-4 c) amination of compound of general formula-4 by reacting it with a compound of general formula-5

Formula-5 wherein, 'P' represents amine protecting group;
in presence of a suitable base in a suitable solvent optionally in presence of a suitable alkali metal halide to provide compound of general formula-6, Formula-6

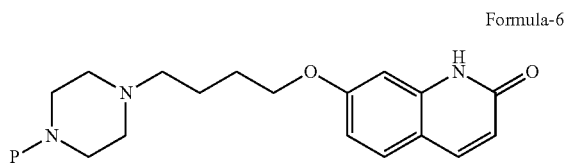

d) deprotecting the compound of general formula-6 with a suitable amine deprotecting agent in a suitable solvent to provide 7-(4-(piperazin-1-yl)butoxy)quinolin-2(1H)-one compound of formula-7 or its salt, Formula-7

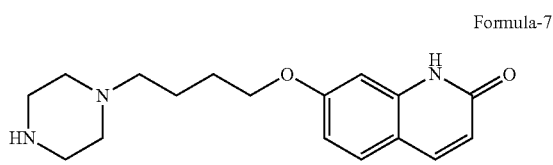

e) reacting the compound of formula-7 or its salt with compound of general formula-8

Formula-8

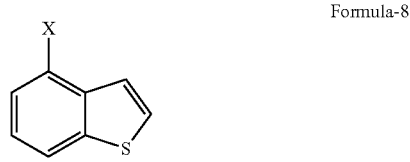

wherein, 'X' is as defined above;
under suitable conditions in a suitable solvent to provide compound of formula-1,
f) purifying the compound of formula-1 from a suitable solvent or mixture of solvents to provide pure compound of formula-1.

Wherein, in step-a) the suitable oxidizing agent is same as defined above;

In step-b) & step-c) the suitable base is selected from organic bases, inorganic bases, organosilicon bases, organolithium bases or their mixtures;

In step-c) the suitable alkali metal halide is selected from NaCl, NaBr, NaI, KCl, KBr, KI, CsCl, CsBr, CsI and the like;

In step-d) the suitable deprotecting agent is selected based on the protecting group employed and can be selected from acids, bases and hydrogenating agents as described above;

In step-e) the reaction can be carried out in the presence of (a) a palladium compound and a tertiary phosphine or (b) a palladium carbene complex, in an inert solvent or without a solvent optionally in presence of a suitable base.

Wherein, the palladium compound is at least one member selected from the group consisting of sodium hexachloropalladate(IV)tetrahydrate, potassium hexachloro palladate(IV), palladium(II) chloride, palladium(II) bromide, palladium(II) acetate, palladium(II) acetylacetonate, dichlorobis(benzonitrile)palladium(II), dichloro bis (acetonitrile)palladium(II), dichlorobis(triphenylphosphine)palladium(II), dichloro tetraamminepalladium(II), dichloro(cycloocta-1,5-diene)palladium(II), palladium(II) trifluoroacetate, tris(dibenzylideneacetone)dipalladium (0), tris(dibenzylideneacetone) dipalladium (0) chloroform complex, tetrakis(triphenyl phosphine)palladium (0) and the like;

The tertiary phosphine can be selected from but not limited to trialkylphosphines such as triethylphosphine, tricyclohexylphosphine, tri-isopropylphosphine, tri-n-butyl phosphine, tri-iso-butylphosphine, tri-sec-butylphosphine, and tri-tert-butyl phosphine; triarylphosphines such as triphenylphosphine, tri-pentafluorophenylphosphine, tri-o-tolylphosphine, tri-m-tolylphosphine, and tri-p-tolylphosphine; phenoxyphosphines such as tri(2,6-dimethylphenoxy)phosphine, tri(2-tert-butylphenoxy) phosphine, triphenoxy phosphine, tri(4-methylphenoxy) phosphine, and tri(2-methylphenoxy)phosphine; and biarylphosphines such as 2,2'-bis(diphenylphosphino)-1,1'-binaphthyl (racemic body), (R)-(+)-2,2'-bis(diphenylphosphino)-1,1'-binaphthyl, and (S)-(+)-2,2'-bis(diphenyl phosphino)-1,1'-binaphthyl, 2-(di-tert-butylphosphino)-1,1'-biphenyl (JohnPhos), 2-dicyclohexylphosphino-2'-methylbiphenyl (MePhos), 2-dicyclohexylphosphino-2',6'-dimethoxy-1,1'-biphenyl (SPhos), 2-(dicyclohexylphosphino)-2'-(N,N-dimethylamino) biphenyl (DavePhos), and 2-(dicyclohexylphosphino)-2',6'-di-iso-propoxy-1,1'-biphenyl (RuPhos). These tertiary phosphines can be used singly or in combination of two or more;

The Palladium carbene complex can be selected from (1,4-naphthoquinone)-[1,3-bis(2,6-diisopropylphenyl)imidazol-2-ylidene]palladium (0), (1,4-naphthoquinone)-[1,3-bis(2,4,6-trimethylphenyl)imidazol-2-ylidene]palladium (0), allylchloro-[1,3-bis(2,6-diisopropylphenyl)imidazol-2-ylidene]palladium (II), allylchloro-[1,3-bis(2,4,6-trimethyl phenyl)imidazol-2-ylidene]palladium (II), allylchloro-[1,3-bis(2,6-diisopropylphenyl)-4,5-dihydroimidazol-2-ylidene-]palladium (II), (3-phenylallylchloro)-[1,3-bis(2,4,6-trimethylphenyl)-imidazol-2-ylidene]palladium (II), (3-phenylallylchloro)-[1,3-bis(2,6-diisopropylphenyl)-4,5-dihydroimidazol-2-ylidene]palladium (II), dichloro-[1,3-bis (2,6-diisopropylphenyl)imidazol-2-ylidene]palladium (II) dimer, and other palladium complexes of N-heterocyclic carbene. These palladium carbene complexes can be used singly or in combination of two or more.

Examples of inert solvents include water, ether solvents such as dioxane, tetrahydrofuran, diethyl ether, diethylene glycol dimethyl ether, and ethylene glycol dimethyl ether; hydrocarbon solvents such as benzene, toluene, and xylene; alcohol solvents such as methanol, ethanol, and isopropanol; ketone solvents such as acetone and methyl ethyl ketone; and polar-aprotic solvents such as dimethylformamide, dimethylsulfoxide; acetonitrile or mixtures thereof.

The suitable base is selected from organic bases, inorganic bases, organosilicon bases, organolithium bases or their mixtures;

In step-a) to step-f) the suitable solvent is selected from hydrocarbon solvents, ether solvents, ester solvents, polar-aprotic solvents, chloro solvents, ketone solvents, nitrile solvents, alcohol solvents, polar solvents, formic acid, acetic acid or mixtures thereof.

The compound of formula-2, compound of general formula-5 and compound of general formula-8 which are utilized in the present invention can be synthesized by any of the known processes or they can be procured from any of the commercial sources.

The embodiment of the present invention provides a process for the preparation of 7-(4-(piperazin-1-yl)butoxy) quinolin-2(1H)-one compound of formula-7 or its salt, a useful intermediate in the preparation of compound of formula-1 comprising of;

a) oxidizing the 7-hydroxy-3,4-dihydroquinolin-2(1H)-one compound of formula-2 with a suitable oxidizing agent in a suitable solvent to provide 7-hydroxyquinolin-2(1H)-one compound of formula-3,
b) reacting the compound of formula-3 with 1,4-disubstituted butane having the following structural formula

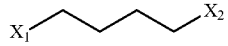

wherein, 'X$_1$', 'X$_2$' have the meaning as defined above; in presence of a suitable base in a suitable solvent to provide compound of general formula-4,

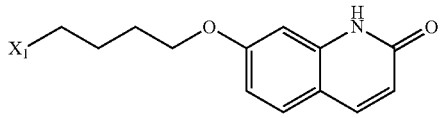

Formula-4 c) amination of compound of general formula-4 by reacting it with a compound of general formula-5

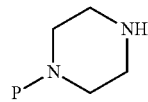

Formula-5 wherein, 'P' represents amine protecting group;
in presence of a suitable base in a suitable solvent optionally in presence of a suitable alkali metal halide to provide compound of general formula-6,

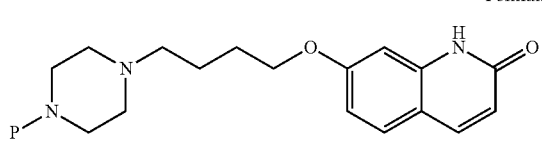

Formula-6 d) deprotecting the compound of general formula-6 with a suitable amine deprotecting agent in a suitable solvent to provide 7-(4-(piperazin-1-yl)butoxy)quinolin-2(1H)-one compound of formula-7 or its salt, The second aspect of the present invention provides a process for the preparation of 7-hydroxyquinolin-2(1H)-one compound of formula-3, comprising of oxidizing the 7-hydroxy-3,4-dihydroquinolin-2(1H)-one compound of formula-2 with a suitable oxidizing agent in a suitable solvent to provide compound of formula-3.

Wherein, the suitable oxidizing agent and the suitable solvent are same as defined in step-a) of the first aspect of the present invention.

The third aspect of the present invention provides an improved process for the preparation of compound of formula-1, comprising of;
a) reacting the 7-hydroxyquinolin-2(1H)-one compound of formula-3 with compound of general formula-26

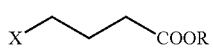

Formula-26 wherein, 'X' represents halogen; 'R' represents C$_1$-C$_6$ straight chain or branched chain alkyl groups;
in presence of a suitable base in a suitable solvent to provide compound of general formula-27,

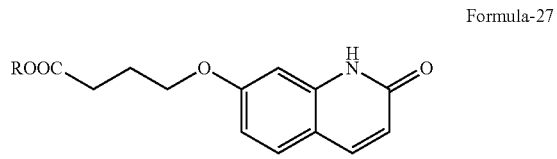

Formula-27 b) hydrolyzing the compound of general formula-27 in presence of a suitable acid or a suitable base optionally in presence of a suitable solvent to provide 4-(2-oxo-1,2-dihydroquinolin-7-yloxy)butanoic acid compound of formula-28,

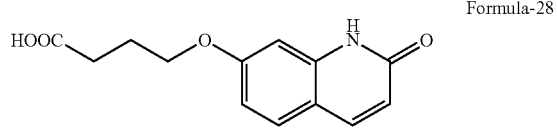

Formula-28 c) reacting the compound of formula-28 with 1-(benzo[b]thiophen-4-yl)piperazine compound of formula-11 or its salt in presence of a suitable base in a suitable solvent optionally in presence of a suitable coupling agent to provide 7-(4-(4-(benzo[b]thiophen-4-yl)piperazin-1-yl)-4-oxobutoxy)quinolin-2(1H)-one compound of formula-29,

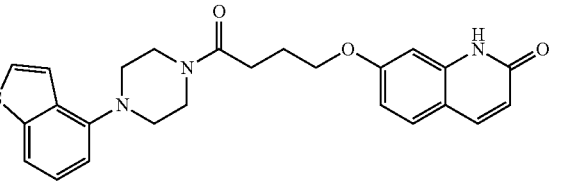

Formula-29 d) reducing the compound of formula-29 with a suitable reducing agent in a suitable solvent to provide compound of formula-1.

Wherein, in step-a) & step-c) the suitable base is selected from inorganic bases, organic bases, organosilicon bases, organolithium bases or their mixtures;
In step-b) the suitable acid is selected from inorganic acids and the suitable base is selected from inorganic bases;
In step-c) the suitable coupling agent is same as defined above;
In step-d) the suitable reducing agent is selected from borane-DMS, borane-THF, lithium aluminium hydride (LiAlH$_4$), Aluminium hydride (AlH$_3$), diisobutylaluminium hydride (DIBAL), NaAlH(O-t-Bu)$_3$, Na(AcO)$_3$BH, B$_2$H$_6$, sodium bis(2-methoxyethoxy) aluminumhydride (Red-Al or Vitride), catalytic hydrogenation in presence of Pd, Pt, Rh, Raney Ni, PtO$_2$ and the like.
In step-a) to step-d) the suitable solvent is same as defined in step-a) of the first aspect of the present invention.

An embodiment of the present invention provides 7-(4-(4-(benzo[b]thiophen-4-yl)piperazin-1-yl)-4-oxobutoxy)quinolin-2(1H)-one compound represented by the following structural formula;

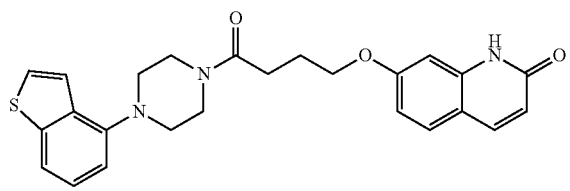 [SMILES: O=C(CCCOc1ccc2ccc(=O)[nH]c2c1)N1CCN(c2cccc3sccc23)CC1]

The other embodiment of the present invention provides use of 7-(4-(4-(benzo[b]thiophen-4-yl)piperazin-1-yl)-4-oxobutoxy)quinolin-2(1H)-one compound of formula-29 as an intermediate for the synthesis of compound of formula-1.

The fourth aspect of the present invention provides a process for the purification of compound of formula-1, comprising of;
a) providing a solution of compound of formula-1 in a suitable solvent or mixture of solvents,
b) optionally treating the reaction mixture with charcoal,
c) combining the solution with a suitable anti-solvent and optionally cooling the reaction mixture to provide pure compound of formula-1.

Wherein, in step-a) the suitable solvent is selected from polar-aprotic solvents, alcohol solvents, chloro solvents or mixtures thereof;

After combining the solution of step-a) or step-b) with anti-solvent the reaction mixture can optionally be cooled to suitable temperature ranges from −25° C. to 25° C.

In the above process, the suitable solvent is preferably selected from polar-aprotic solvents and the suitable anti solvent is preferably polar solvent.

In one embodiment, the suitable solvent is preferably dimethyl sulfoxide and the suitable anti-solvent is water.

A preferred embodiment of the present invention provides a process for the purification of compound of formula-1, comprising of;
a) dissolving the compound of formula-1 in dimethyl sulfoxide,
b) optionally treating the reaction mixture with charcoal,
c) combining the solution with pre-heated water,
d) cooling the reaction mixture,
e) filtering the solid and drying to provide pure compound of formula-1.

The above process produces highly pure compound of formula-1 with excellent yield. All the related substances and residual solvents are controlled well within the limits as suggested by ICH.

The formation of following compounds as impurities in compound of formula-1 has been observed during the synthesis of compound of formula-1 by the process of the present invention.

| Name of the impurity | Structure |
| --- | --- |
| Piperazine quinoline impurity | 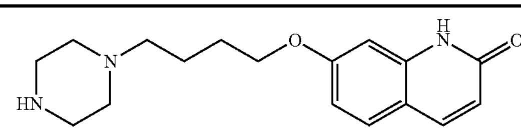 |
| Piperazine butoxy dimer impurity | 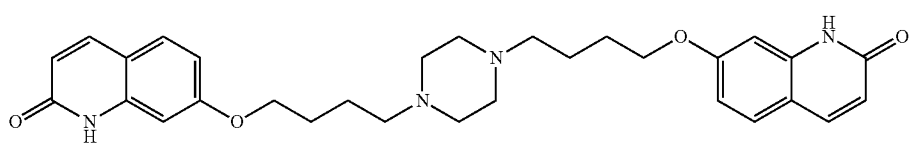 [SMILES: O=c1ccc2ccc(OCCCCN3CCN(CCCCOc4ccc5ccc(=O)[nH]c5c4)CC3)cc2[nH]1] |
| Bromo benzothiophene impurity | 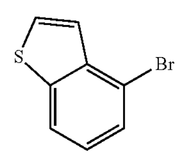 |

Providing a solution of compound of formula-1 in a suitable solvent or mixture of solvents can be done by dissolving the compound of formula-1 in said solvent or mixture of solvents at a suitable temperature ranges from 25° C. to 100° C. or the solution can be obtained directly from the synthetic process in which compound of formula-1 is prepared;

Step-b) can be carried out at a suitable temperature ranges from 25° C. to 100° C.;

In step-c) the suitable anti-solvent is selected from polar solvents, hydrocarbon solvents, ether solvents, ester solvents, ketone solvents, nitrile solvents or mixtures thereof; and combining the solution of step-a) or step-b) with anti-solvent can be carried out at a suitable temperature ranges from 0° C. to 100° C.

In this step, before combining the solution with anti-solvent, the anti-solvent can optionally be heated to a suitable temperature ranges from 35° C. to 100° C.;

All these impurities were identified, characterized and well controlled within the limits in API. Even some of the impurities are not detected in the final drug substance. Hence, the above process is highly advantageous on industrial scale to prepare compound of formula-1 with high yield and quality to meet the regulatory requirements.

An embodiment of the present invention provides compound of formula-1 substantially free of above said impurities. i.e., the content of any of the above said impurities in compound of formula-1 is less than 0.15%, preferably less than 0.1%, more preferably less than 0.05%, most preferably less than 0.03% by HPLC.

The other embodiment of the present invention provides compound of formula-1 which is completely free of any of the above said impurities.

The fifth aspect of the present invention provides a process for the preparation of crystalline form-I of 7-{4-[4-

(1-benzothiophen-4-yl)piperazin-1-yl]butoxy}quinolin-2 (1H)-one hydrochloride compound of formula-1a, comprising of;
a) adding hydrochloric acid to compound of formula-1 in a suitable alcohol solvent,
b) heating the reaction mixture to a suitable temperature,
c) cooling the reaction mixture to a suitable temperature,
d) filtering the solid to provide crystalline form-I of compound of formula-1a.

Wherein, in step-a) the suitable alcohol solvent is selected from but not limited to methanol, ethanol, n-propanol, iso-propanol, n-butanol, iso-butanol, 2-butanol, tert-butanol, ethane-1,2-diol, propane-1,2-diol or their mixtures;

In step-b) the suitable temperature ranges from 30° C. to reflux temperature of the solvent used;

In step-c) the suitable temperature ranges from −50° C. to 30° C.

The sixth aspect of the present invention provides a process for the purification of compound of formula-1a, comprising of;
a) adding a suitable solvent to compound of formula-1a,
b) heating the reaction mixture to a suitable temperature,
c) cooling the reaction mixture to a suitable temperature,
d) filtering the solid to provide pure compound of formula-1a.

Wherein, in step-a) the suitable solvent is selected from but not limited to alcohol solvents, ether solvents, ester solvents, chloro solvents, hydrocarbon solvents, ketone solvents, polar solvents, polar-aprotic solvents, nitrile solvents or their mixtures;

In step-b) the suitable temperature ranges from 30° C. to reflux temperature of the solvent used; and in step-c) the suitable temperature ranges from −50° C. to 30° C.

The seventh aspect of the present invention provides another process for the purification of compound of formula-1a, comprising of;
a) adding a suitable solvent to compound of formula-1a at a suitable temperature,
b) stirring the reaction mixture for a suitable time,
c) optionally cooling the reaction mixture to a suitable temperature,
d) filtering the solid to provide pure compound of formula-1a.

Wherein, in step-a) the suitable solvent is same as defined in step-a) of the sixth aspect of the present invention; and the suitable temperature is 25-30° C.;

In step-b) the suitable time ranges from 5 min to 15 hrs;

In step-c) the suitable temperature ranges from −50° C. to 20° C.

The eighth aspect of the present invention provides a process for the preparation of compound of formula-1, comprising of;
a) providing a solution of acid-addition salt of compound of formula-1 in a suitable solvent,
b) optionally treating the reaction mixture with charcoal at a suitable temperature,
c) adding aqueous ammonia solution to the reaction mixture at a suitable temperature to provide compound of formula-1.

Wherein, in step-a) the acid is selected from but not limited to hydrochloric acid, hydrobromic acid, hydroiodic acid, nitric acid, phosphoric acid, sulfuric acid, acetic acid, formic acid, propionic acid, oxalic acid, succinic acid, fumaric acid, malonic acid, malic acid, maleic acid, tartaric acid, citric acid, methanesulfonic acid, ethanesulfonic acid, benzenesulfonic acid, p-toluenesulfonic acid, palmitic acid, stearic acid, aspartic acid, ascorbic acid, 2-oxopropionic acid (pyruvic acid), furan-2-carboxylic acid (mucic acid), benzoic acid, 4-hydroxybenzoic acid, salicylic acid, vanillic acid, 4-hydroxycinammic acid, phthalic acid, mandelic acid, acetyl mandelic acid and the like; the suitable acid is preferably hydrochloric acid.

The suitable solvent is same as defined in step-a) of the sixth aspect of the present invention;

In step-b) the suitable temperature ranges from 25° C. to reflux temperature of the solvent used; and in step-c) the suitable temperature ranges from −30° C. to reflux temperature of the solvent used.

In the above process, after adding the aqueous ammonia solution, the reaction mixture can optionally be heated to a suitable temperature ranges from 30° C. to reflux temperature of the solvent used and then cooled to lower temperatures ranges from −50° C. to 30° C.

Further in step c) instead of ammonia other inorganic bases also useful for the preparation of compound of formula-1 from it's corresponding acid addition salts. The suitable inorganic bases can be selected form but not limited to alkali metal carbonates, alkali metal bicarbonates; alkali metal hydroxides; alkali metal alkoxides;

The ninth aspect of the present invention provides a process for the preparation of crystalline compound of formula-1, comprising of;
a) suspending the compound of formula-1 in a suitable solvent at a suitable temperature, characterized in that the compound is not dissolved in the solvent at the said temperature,
b) optionally cooling the reaction mixture to a suitable temperature and filtering the solid to provide crystalline compound of formula-1.

Wherein, in step-a) the suitable solvent is same as defined in step-a) of the sixth aspect of the present invention; the suitable temperature ranges from −30° C. to reflux temperature of the solvent used; in step-b) suitable temperature ranges from −50° C. to 30° C.

An embodiment of the present invention provides a process for the preparation of crystalline compound of formula-1, comprising of;
a) suspending the compound of formula-1 in methanol at 60-65° C.,
b) cooling the reaction mixture to 25-30° C. and filtering the solid to provide crystalline compound of formula-1.

The tenth aspect of the present invention provides alternate process for the preparation of crystalline compound of formula-1, comprising of;
a) providing a solution of compound of formula-1 in a suitable solvent,
b) distilling off the solvent from the reaction mixture optionally under reduced pressure to provide crystalline compound of formula-1.

Wherein, in step-a) the suitable solvent is same as defined in step-a) of the sixth aspect of the present invention.

In one embodiment, the suitable solvent is preferably selected from alcohol solvents. The suitable solvent is preferably methanol.

An embodiment of the present invention provides a process for the preparation of crystalline compound of formula-1, comprising of;
a) providing a solution of compound of formula-1 in methanol,
b) distilling off the solvent from the reaction mixture to provide crystalline compound of formula-1.

Figure 5:
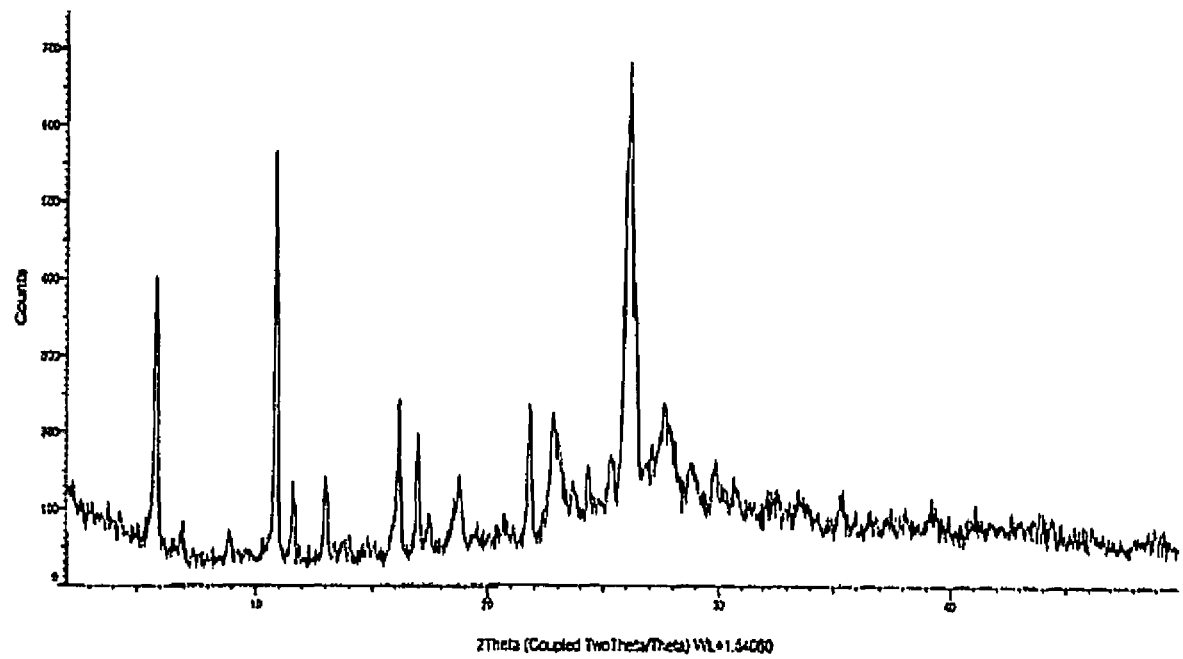

The eleventh aspect of the present invention provides novel crystalline polymorph of 7-{4-[4-(1-benzothiophen-4-yl)piperazin-1-yl]butoxy}quinolin-2(1H)-one hydrochloride compound of formula-1a, herein after designated as form-II. The said crystalline form is characterized by its PXRD pattern having characteristic peaks at 5.8, 10.8, 11.6, 12.9, 16.1, 16.9, 18.7, 21.7, 22.7, 26.0 and 27.6±0.2° of 2-theta and is further characterized by its PXRD pattern as illustrated in FIG. 5.

The twelfth aspect of the present invention provides a process for the preparation of crystalline form-II of compound of formula-1a, comprising of;
a) adding hydrochloric acid to a solution of compound of formula-1 in dichloromethane,
b) adding methanol to the reaction mixture,
c) filtering the solid to provide crystalline form-II of compound of formula-1a.

Figure 6:
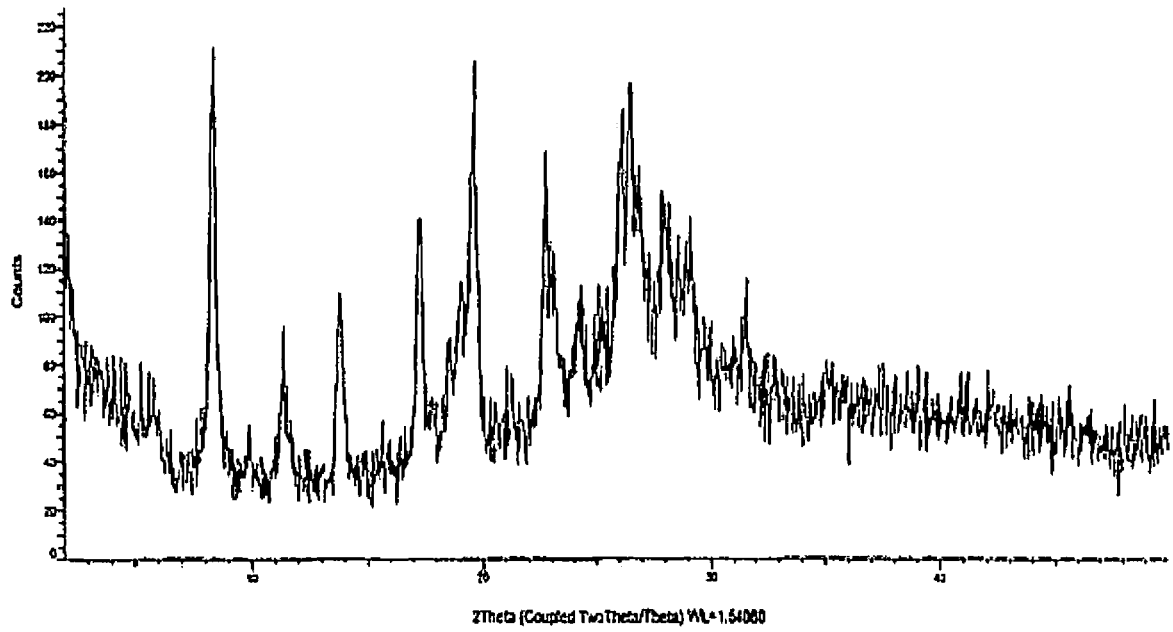

The thirteenth aspect of the present invention provides novel crystalline polymorph of compound of formula-1a, herein after designated as form-III. The said polymorph is characterized by its PXRD pattern having characteristic peaks at 8.3, 11.3, 13.7, 17.2, 19.5, 22.7 and 26.4±0.2° of 2-theta and is further characterized by its PXRD pattern as illustrated in FIG. 6.

The fourteenth aspect of the present invention provides a process for the preparation of crystalline form-III of compound of formula-1a, comprising of;
a) adding methanol to the compound of formula-1a,
b) slowly adding hydrochloric acid to the reaction mixture,
c) filtering the solid to provide crystalline form-III of compound of formula-1a.

The fifteenth aspect of the present invention provides a process for the preparation of 7-{4-[4-(1-benzothiophen-4-yl)piperazin-1-yl]butoxy}quinolin-2(1H)-one compound of formula-1, comprising of;
a) reacting the 7-hydroxy-3,4-dihydroquinolin-2(1H)-one compound of formula-2 with 1,4-disubstituted butane having the following structural formula

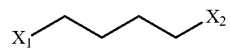

wherein, 'X$_1$', 'X$_2$' have the meaning as defined above;
in presence of a suitable base in a suitable solvent to provide compound of general formula-9,

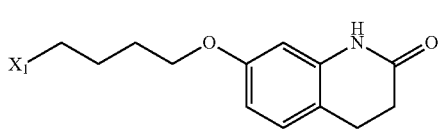

Formula-9 b) reacting the compound of general formula-9 with 1-(benzo[b]thiophen-4-yl)piperazine compound of formula-11 or its salt

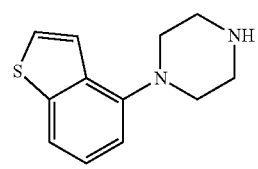

Formula-11 in presence of a suitable base in a suitable solvent optionally in presence of a suitable alkali metal halide to provide 7-{4-[4-(1-benzothiophen-4-yl)piperazin-1-yl]butoxy}-3,4-dihydroquinolin-2(1H)-one compound of formula-12,

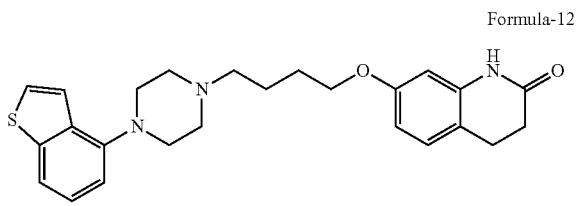 [SMILES: O=C1CCc2ccc(OCCCCN3CCN(c4cccc5sccc45)CC3)cc2N1]

Formula-12 c) oxidizing the compound of formula-12 in presence of a suitable oxidizing agent in a suitable solvent to provide compound of formula-1.

Wherein, in step-a) & step-b) the suitable base is selected from organic bases, inorganic bases, organosilicon bases, organolithium bases or their mixtures;
In step-b) the suitable alkali metal halide is selected from NaCl, NaBr, NaI, KCl, KBr, KI, CsCl, CsBr, CsI and the like;
In step-c) the suitable oxidizing agent is same as defined in step-a) of the first aspect of the present invention;
In step-a) to step-c) the suitable solvent is same as defined in step-a) of the first aspect of the present invention.

The sixteenth aspect of the present invention provides another process for the preparation of compound of formula-1, comprising of;
a) halogenation of compound of general formula-9 with a suitable halogenating agent optionally in presence of a suitable solvent to provide compound of general formula-10,

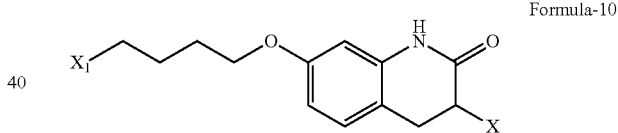

Formula-10 b) dehydrohalogenation of compound of general formula-10 by treating it with a suitable base in a suitable solvent to provide compound of general formula-4,
c) reacting the compound of general formula-4 with 1-(benzo[b]thiophen-4-yl)piperazine compound of formula-11 or its salt in presence of a suitable base in a suitable solvent optionally in presence of a suitable alkali metal halide to provide compound of formula-1.

Wherein, in step-a) the suitable halogenating agent is selected from Cl$_2$, Br$_2$, I$_2$, HCl, HBr, SOCl$_2$, PCl$_3$, PBr$_3$, PCl$_5$, POCl$_3$, N-chlorosuccinimide (NCS), N-bromosuccinimide (NBS), N-iodosuccinimide (NIS) and the like;
In step-b) the dehydrohalogenation reaction can be carried out in presence of a suitable strong base selected from alkali metal hydroxides, alkali metal alkoxides, alkali metal amides, organic bases and the like;
In step-c) the suitable alkali metal halide and the suitable base are same as defined in step-c) of the first aspect of the present invention;
In step-a) to step-c) the suitable solvent is same as defined in step-a) of the first aspect of the present invention.

An embodiment of the present invention provides a process for the preparation of compound of general formula-4, comprising of oxidizing the compound of general formula-9 with an oxidizing agent in a suitable solvent to provide compound of general formula-4.

Wherein, the suitable oxidizing agent and the suitable solvent are same as defined in step-a) of the first aspect of the present invention.

The seventeenth aspect of the present invention provides alternative process for the preparation of compound of formula-1, comprising of;

a) reacting the compound of general formula-5 with 1,4-disubstituted butane having the following structural formula

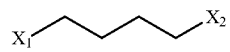

wherein, '$X_1$', '$X_2$' have the meaning as defined above; in presence of a suitable base in a suitable solvent optionally in presence of a suitable alkali metal halide to provide compound of general formula-13,

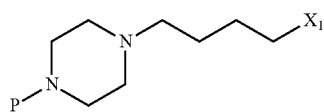

Formula-13 b) deprotecting the compound of general formula-13 with a suitable amine deprotecting agent in a suitable solvent to provide compound of general formula-14,

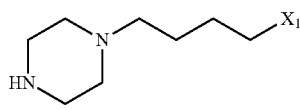

Formula-14 c) reacting the compound of general formula-14 with compound of general formula-8 under suitable conditions to provide compound of general formula-15,

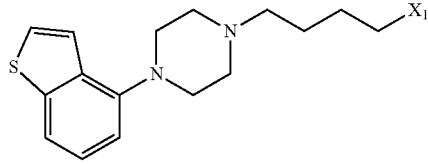

Formula-15 d) reacting the compound of general formula-15 with 7-hydroxyquinolin-2(1H)-one compound of formula-3 in presence of a suitable base in a suitable solvent to provide compound of formula-1.

Wherein, in step-a) the suitable base and the suitable alkali metal halide are same as defined in step-c) of the first aspect of the present invention;

In step-b) the suitable amine deprotecting agent is same as defined in step-d) of the first aspect of the present invention;

Step-c) can be carried out in a similar manner to step-e) of the first aspect of the present invention;

In step-d) the suitable base can be selected from organic bases, inorganic bases, organolithium bases, organosilicon bases or mixtures thereof;

In step-a) to step-d) the suitable solvent is same as defined in step-a) of the first aspect of the present invention.

The eighteenth aspect of the present invention provides another process for the preparation of compound of formula-1, comprising of;

a) reacting the 1-(benzo[b]thiophen-4-yl)piperazine compound of formula-11 or its salt with 1,4-disubstituted butane having the structural formula

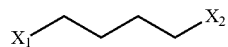

wherein, '$X_1$', '$X_2$' have the meaning as defined above; in presence of a suitable base in suitable solvent optionally in presence of a suitable alkali metal halide to provide compound of general formula-15, b) reacting the compound of general formula-15 with 7-hydroxy-3,4-dihydroquinolin-2(1H)-one compound of formula-2 in presence of a suitable base in a suitable solvent to provide 7-{4-[4-(1-benzothiophen-4-yl)piperazin-1-yl]butoxy}-3,4-dihydroquinolin-2(1H)-one compound of formula-12, c) oxidizing the compound of formula-12 with a suitable oxidizing agent in a suitable solvent to provide compound of formula-1.

Wherein, in step-a) the suitable base and the suitable alkali metal halide are same as defined in step-c) of the first aspect of the present invention;

In step-b) the suitable base can be selected from organic bases, inorganic bases, organolithium bases, organosilicon bases or mixtures thereof;

In step-c) the suitable oxidizing agent is same as defined in step-a) of the first aspect of the present invention;

In step-a) to step-c) the suitable solvent is same as defined in step-a) of the first aspect of the present invention.

The nineteenth aspect of the present invention provides alternative process for the preparation of compound of formula-1, comprising of;

a) reacting the compound of general formula-16

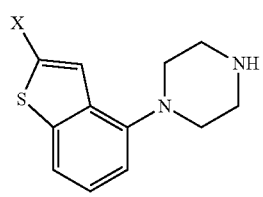

Formula-16 wherein, 'X' is as defined above;

with compound of general formula-4 in presence of a suitable base in a suitable solvent optionally in presence of a suitable alkali metal halide to provide compound of general formula-17,

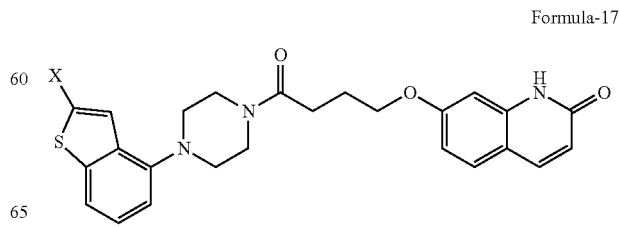

Formula-17 b) dehalogenation of compound of general formula-17 with a suitable dehalogenating agent in a suitable solvent to provide compound of formula-1.

Wherein, in step-a) the suitable base and the suitable alkali metal halide are same as defined in step-c) of the first aspect of the present invention;

In step-b) the suitable dehalogenating agent can be selected from but not limited to Raney Ni, Pd—C, PdCl$_2$, NaBH$_4$ and the like;

In step-a) to step-b) the suitable solvent is same as defined in step-a) of the first aspect of the present invention.

An embodiment of the present invention provides a process for the preparation of compound of formula-1, comprising of;

a) reacting the 1-(benzo[b]thiophen-4-yl)piperazine compound of formula-11 or its salt with compound of general formula-24

Formula-24

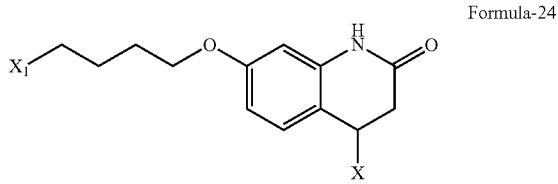

wherein, 'X$_1$', 'X' have the meaning as defined above;
in presence of a suitable base in a suitable solvent optionally in presence of a suitable alkali metal halide to provide compound of general formula-25, Formula-25

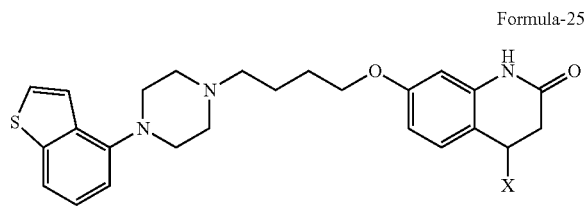

b) dehydrohalogenation of compound of general formula-25 in presence of a suitable base in a suitable solvent to provide compound of formula-1.

Wherein, in step-a) the suitable base and the suitable alkali metal halide are same as defined in step-c) of the first aspect of the present invention;

In step-b) the dehydrohalogenation reaction can be carried out in the same manner as that described in step-b) of the sixteenth aspect of the present invention.

The decarboxylation of compound of formula-33 to compound of formula-12 as described in scheme-VII of the present invention can be carried out in presence of a catalyst selected from copper, cuprous oxide, copper oxide, chromium trioxide, cuprous bromide, cuprous chloride, ferrous chloride, ferric chloride, copper carbonate, copper sulfate, basic copper carbonate, silver acetate, calcium oxide, calcium hydroxide, alumina, silver carbonate, acids such as acetic acid, hydrochloric acid, quinol optionally in combination with Cu and the like optionally in presence of a suitable solvent as defined above.

The compound of formula-1 and its various intermediate compounds of the present invention can be prepared by the processes as illustrated in schemes-I to VII given below in analogous manner to the procedures described herein before or by the processes known to a person skilled in the art to prepare such type of compounds or to carry out such type of chemical conversions.

The compound of formula-1 produced by various processes of the present invention is having purity of greater than 99%, preferably greater than 99.5%, more preferably greater than 99.7% by HPLC.

It is noted in the art that the particle size of a drug may also affect the release, dissolution, absorption and therapeutic action of pharmaceutical product.

Based on the available literature and knowledge of skilled person in the art, it is evident that apart from various factors, process parameters like temperature, cooling rate, stirring rate and mode of addition of a solvent/anti solvent during crystallization play a major role in the particle size and shape of the product. Likewise the 7-{4-[4-(1-benzothiophen-4-yl)piperazin-1-yl]butoxy}quinolin-2(1H)-one compound of formula-1 also showing different particle size by varying process parameters like temperature, cooling rate, stirring rate and mode of addition of a solvent/anti solvent during crystallization of 7-{4-[4-(1-benzothiophen-4-yl)piperazin-1-yl]butoxy}quinolin-2(1H)-one compound of formula-1.

The compound of formula-1 produced by any of the processes of the present invention can be further micronized or milled to get desired particle size to achieve desired solubility profile based on different forms of pharmaceutical composition requirements. Techniques that may be used for particle size reduction includes but not limited to single or multi-stage micronization using cutting mills, pin/cage mills, hammer mills, jet mills, fluidized bed jet mills, ball mills and roller mills. Milling or micronization may be performed before drying or after drying of the product.

The compound of formula-1 produced by various processes of the present invention is having particle size distribution of D$_{90}$ less than 500 μm, preferably less than 250 μm, more preferably less than 100 μm, most preferably less than 50 μm.

An embodiment of the present invention provides compound of formula-1 with particle size distribution of D$_{90}$ less than 20 μm, preferably less than 10 μm.

PXRD Method of Analysis:

The PXRD analysis of compounds of the present invention was carried out by using BRUKER/D8 ADVANCE X-Ray diffractometer using CuKα radiation of wavelength 1.5406 A° and at a continuous scan speed of 0.03°/min.

HPLC Method of Analysis:

The compound of formula-1 produced by the process of the present invention was analyzed by HPLC under the following conditions;

Apparatus: A liquid chromatograph equipped with variable wavelength UV detector
Column: Kromasil 100 C18, 250×4.6 mm, 5 μm or equivalent
Wavelength: 210 nm
Column temperature: 45° C.
Auto sampler temperature: 5° C.
Injection volume: 5 μL
Diluent: Acetonitrile: Methanol (50:50 v/v)
Elution: Gradient
Buffer preparation: Transfer 1.0 mL of orthophosphoric acid and 3.0 gm of 1-octane sulfonic acid sodium salt in 1000 mL of Milli-Q-water and filter the solution through 0.22 μm Nylon membrane filter paper.
Mobile phase-A: Buffer (100%)
Mobile phase-B preparation: Accurately transfer 700 mL of acetonitrile and 300 mL of buffer into a 1000 mL mobile phase bottle, mix well and sonicate to degas it.

Particle Size Distribution (PSD) Method of Analysis:
The particle size distribution analysis was carried out by using Malvern Mastersizer 3000 instrument.
The present invention is schematically represented as follows.
Scheme-I:
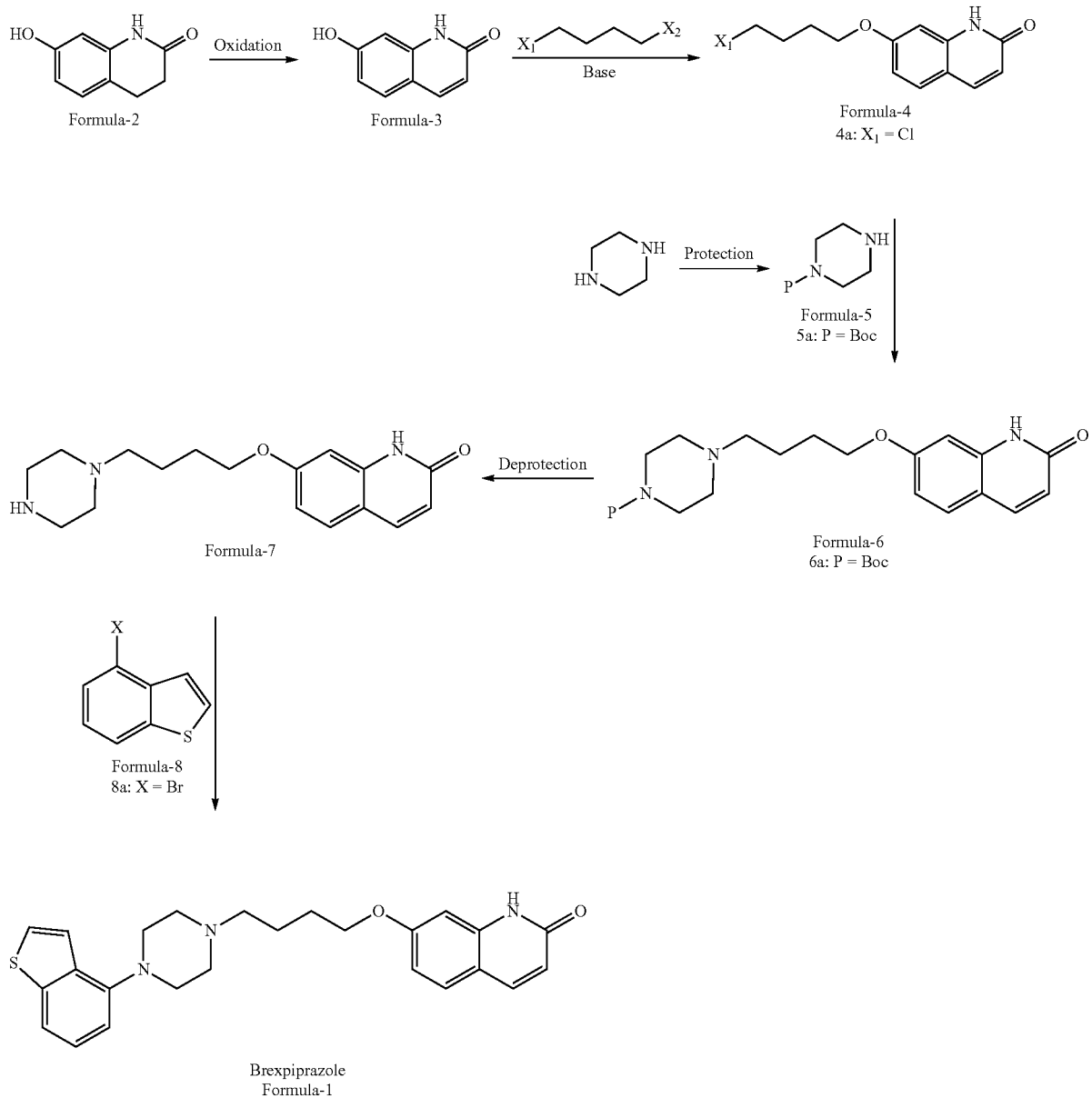
Scheme-II:
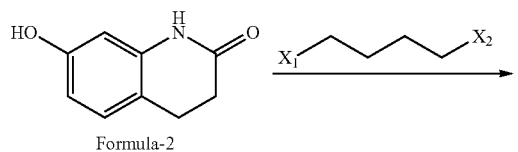

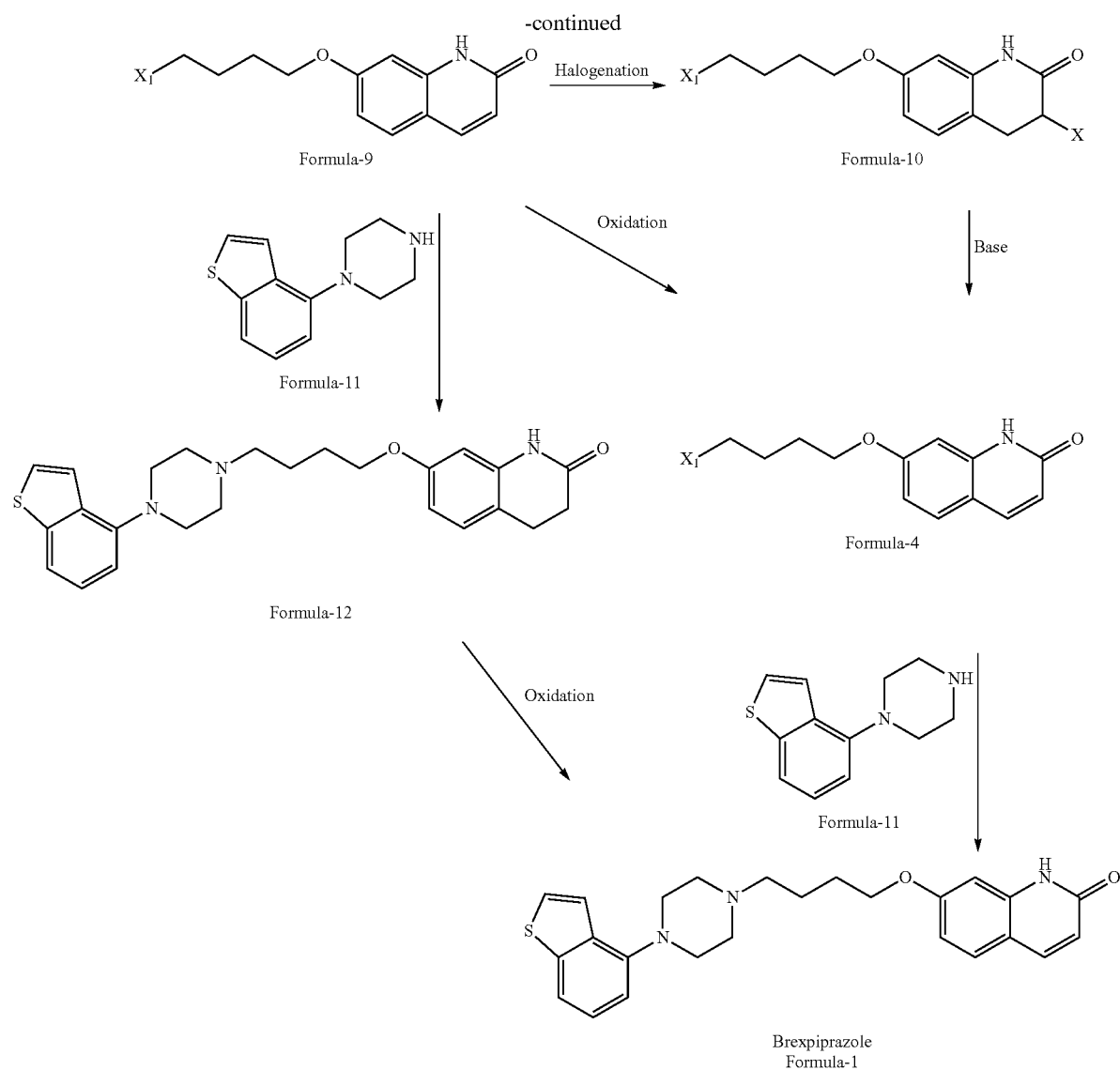
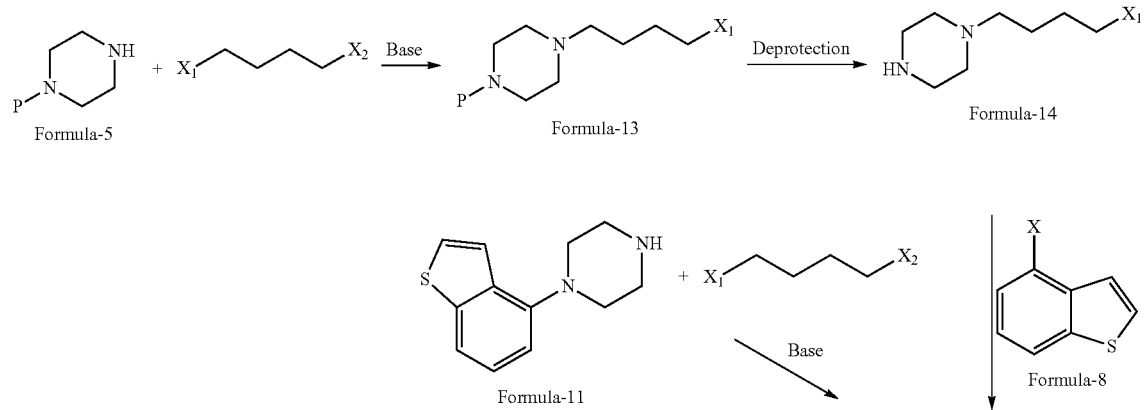
Scheme-III:

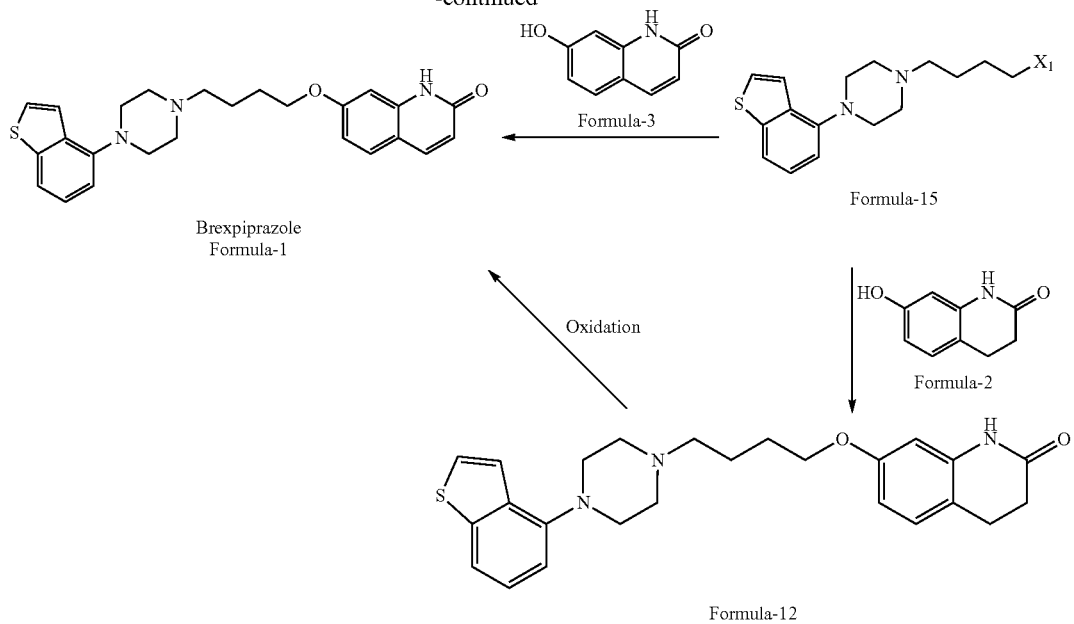
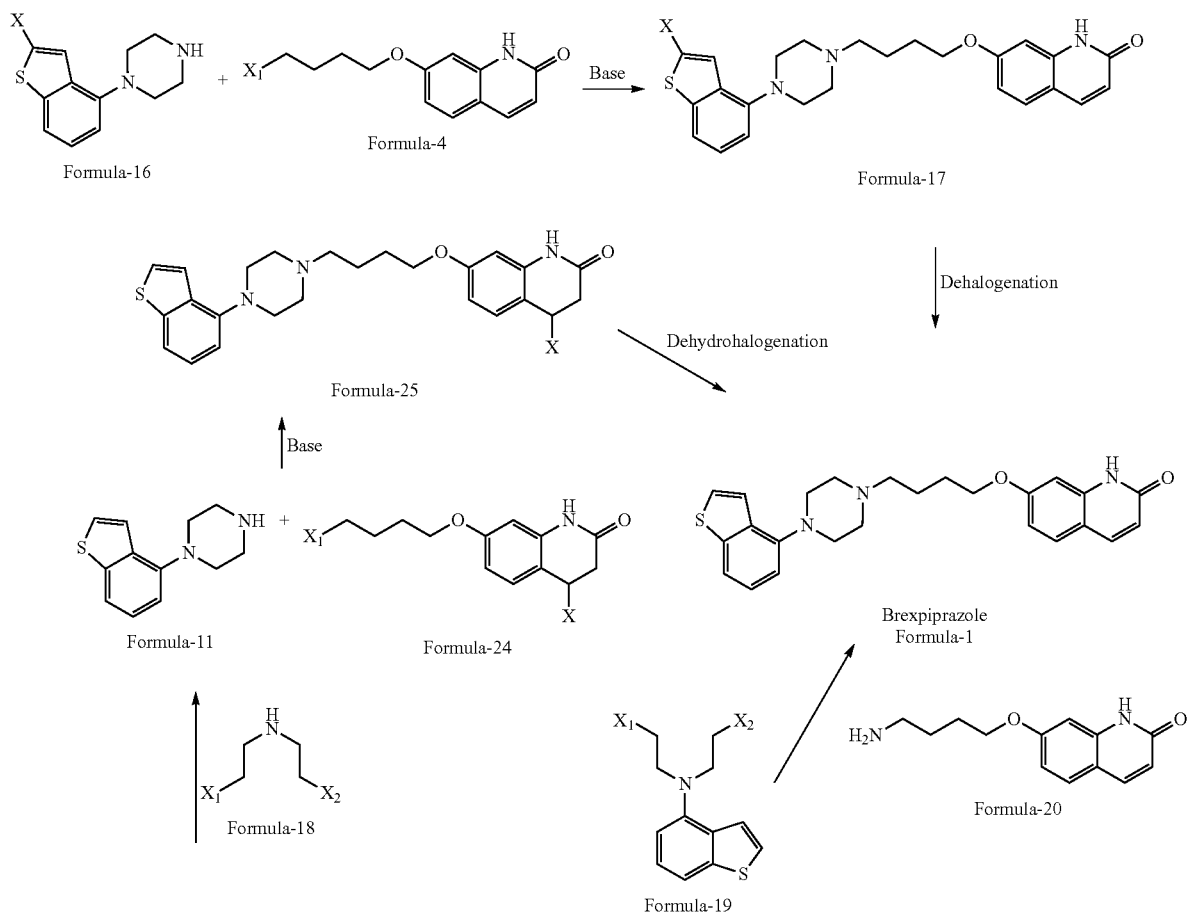
Scheme-IV:

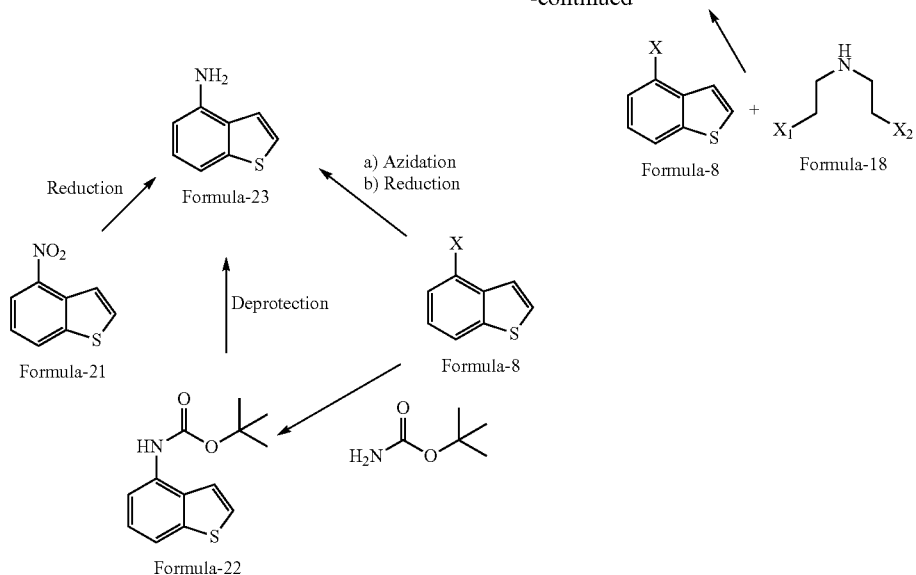
Scheme-V:
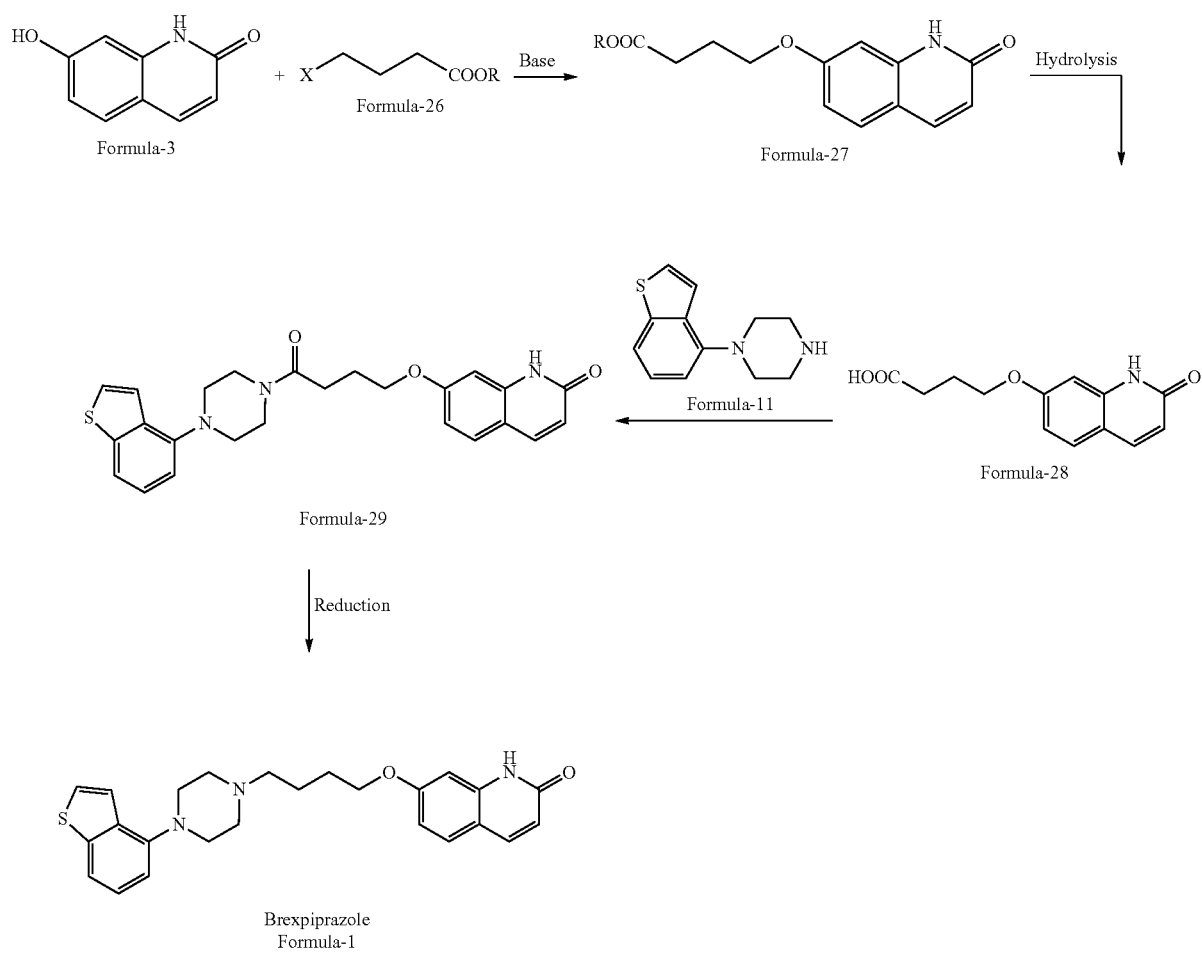

Scheme-VI:

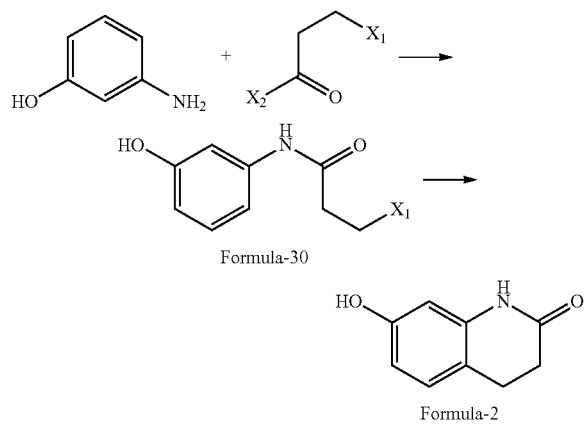

Scheme-VII:

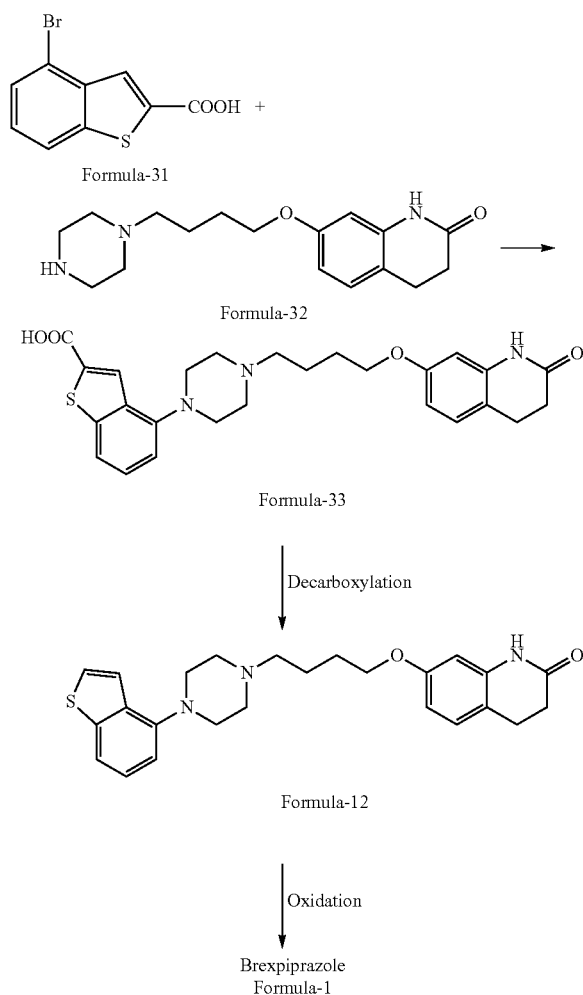

In all the above schemes, the groups 'X$_1$', 'X$_2$' are same or different and can be independently selected from leaving groups such as halogen, substituted/unsubstituted alkyl/aryl sulfonyloxy; 'X' represents halogen such as F, Cl, Br and I; represents C$_1$-C$_6$ straight chain or branched chain alkyl groups; and 'P' represents amine protecting group or N-protecting group.

The best mode of carrying out the present invention is illustrated by the below mentioned examples. These examples are provided as illustration only and hence should not be construed as limitation to the scope of the invention.

EXAMPLES

Example-1: Preparation of 7-hydroxyquinolin-2(1H)-one

A solution of 4,5-dichloro-3,6-dihydroxyphthalonitrile (40.86 gm) in tetrahydrofuran (100 ml) was added to a pre-cooled mixture of 7-hydroxy-3,4-dihydroquinolin-2 (1H)-one (25 gm) and tetrahydrofuran (50 ml) at 0-5° C. and stirred the reaction mixture for 20 min at the same temperature. Raised the temperature of the reaction mixture to 25-30° C. and stirred for 11 hrs at the same temperature. Filtered the solid, washed with tetrahydrofuran and suck dried the material. Methanol (125 ml) was added to the obtained compound at 25-30° C. Heated the reaction mixture to 50-55° C. and stirred for 1 hr at the same temperature. Cooled the reaction mixture to 25-30° C. and stirred for 1 hr at the same temperature. Filtered the solid, washed with methanol and dried the material to get the title compound. Yield: 20.3 gm.

Example-2: Preparation of 7-(4-chlorobutoxy)quinolin-2(1H)-one

Potassium carbonate (60 gm) was added to a mixture of 7-hydroxyquinolin-2(1H)-one (50 gm), dimethylformamide (250 ml) and water (25 ml) at 25-30° C. and stirred the reaction mixture for 10 min at the same temperature. 1-Bromo-4-chlorobutane (106.4 gm) was added to the reaction mixture at 25-30° C. and stirred for 20 hrs at the same temperature. Water and toluene were added to the reaction mixture at 25-30° C. and stirred for 1 hr at the same temperature. Filtered the solid and washed with water. Water (250 ml) was added to the obtained compound at 25-30° C. and stirred for 40 min at the same temperature. Filtered the solid and washed with water. Methyl tert.butyl ether (150 ml) was added to the obtained compound at 25-30° C. Heated the reaction mixture to 50-55° C. and stirred for 1 hr at the same temperature. Cooled the reaction mixture to 0-5° C. and stirred for 1 hr at the same temperature. Filtered the solid, washed with methyl tert.butyl ether and dried the material to get the title compound. Yield: 56.6 gm; M.R: 120-125° C.

Example-3: Preparation of tert-butyl 4-(4-(2-oxo-1, 2-dihydroquinolin-7-yloxy)butyl)piperazine-1-carboxylate A solution of di tert.butyl dicarbonate (27 gm) in methanol (120 ml) was slowly added to a solution of piperazine (21.2 gm) in methanol (120 ml) at 25-30° C. and stirred the reaction mixture for 30 min at the same temperature. Distilled off the solvent completely from the reaction mixture under reduced pressure. Water was added to the obtained compound at 25-30° C. and stirred the reaction mixture for 2 hrs at the same temperature. Filtered the reaction mixture, sodium chloride was added to the filtrate at 25-30° C. and stirred for 15 min at the same temperature. Dichloromethane was added to the reaction mixture at 25-30° C. and stirred for 15 min at the same temperature. Both the organic and aqueous layers were separated and extracted the aqueous layer with dichloromethane. Combined the organic layers and distilled off the solvent completely. Dimethylformamide (60 ml) was added to the obtained compound at 25-30° C. and stirred the reaction mixture for 10 min at the same temperature. 7-(4-Chlorobutoxy)quinolin-2(1H)-one (20 gm), sodium bicarbonate (8.67 gm) and sodium iodide (5.95 gm) were added to the reaction mixture at 25-30° C. Heated the reaction mixture to 90-95° C. and stirred for 7 hrs at the same temperature. Cooled the reaction mixture to 25-30° C., water was added to it and stirred for 3 hrs at the same temperature. Filtered the solid and washed with water. To the obtained solid, water (100 ml) was added at 25-30° C. and stirred the reaction mixture for 1 hr at the same temperature. Filtered the solid, washed with water and dried the material to get the title compound. Yield: 26.4 gm.

Example-4: Preparation of 7-(4-(piperazin-1-yl)butoxy)quinolin-2(1H)-one

A mixture of tert-butyl 4-(4-(2-oxo-1,2-dihydroquinolin-7-yloxy)butyl)piperazine-1-carboxylate (220 gm), isopropyl alcohol (1100 ml) and isopropyl alcohol-HCl (1100 ml) was heated to 75-80° C. and stirred the reaction mixture for 8 hrs at the same temperature. Cooled the reaction mixture to 25-30° C. and stirred for 3 hrs at the same temperature. Filtered the precipitated solid and washed with isopropyl alcohol. Dichloromethane (2200 ml) was added to the obtained compound at 25-30° C. Basified the reaction mixture using aqueous potassium carbonate solution at 25-30° C. and stirred the reaction mixture for 20 min at the same temperature. Both the organic and aqueous layers were separated and extracted the aqueous layer with dichloromethane. Combined the organic layers and distilled off the solvent completely. Cyclohexane (1100 ml) was added to the obtained compound at 25-30° C. and stirred the reaction mixture for 1 hr at the same temperature. Filtered the solid, washed with cyclohexane and dried the material to get the title compound. Yield: 130.0 gm.

Example-5: Alternate Process for the Preparation of 7-(4-(piperazin-1-yl)butoxy) quinolin-2(1H)-one A mixture of tert-butyl 4-(4-(2-oxo-1,2-dihydroquinolin-7-yloxy)butyl)piperazine-1-carboxylate (100 gm), isopropyl alcohol (500 ml) and isopropyl alcohol-HCl (500 ml) was heated to 75-80° C. and stirred the reaction mixture for 4 hrs at the same temperature. Distilled off the solvent from the reaction mixture. Water (1000 ml) was added to the obtained compound at 25-30° C. Cooled the reaction mixture to 5-10° C. and stirred for 90 min at the same temperature. Filtered the reaction mixture through hyflow bed and washed the hyflow bed with water. Dichloromethane (500 ml) was added to the filtrate at 25-30° C. and stirred the reaction mixture for 10 min at the same temperature. Both the organic and aqueous layers were separated and cooled the aqueous layer to 5-10° C. Basified the aqueous layer by using 5% aqueous NaOH solution at 5-10° C. and stirred the reaction mixture for 1 hr at the same temperature. Filtered the solid, washed with isopropyl alcohol and dried the material to get the title compound. Yield: 20.3 gm.

Example-6: Preparation of 7-{4-[4-(1-benzothiophen-4-yl)piperazin-1-yl]butoxy}quinolin-2(1H)-one (Formula-1)

7-(4-(piperazin-1-yl)butoxy)quinolin-2(1H)-one (84.85 gm), 4-bromobenzo[b] thiophene (30 gm), sodium tert.butoxide (67.6 gm) and 1,4-dioxane (300 ml) were charged into a clean and dry RBF at 25-30° C. Purged the reaction mixture with nitrogen gas for 20 min. Pd(OAc)$_2$ (4.04 gm) and BINAP (1.31 gm) were added to the reaction mixture at 25-30° C. Heated the reaction mixture to 110-115° C. and stirred for 15 hrs at the same temperature. Cooled the reaction mixture to 25-30° C., methanol (1000 ml) and acetic acid (75 ml) were added to it. Filtered the reaction mixture through hyflow bed and washed the hyflow bed with methanol. The obtained filtrate was added to water (600 ml) at 25-30° C. Slowly basified the reaction mixture using 5% aq.sodium hydroxide solution. Filtered the solid, washed with water and dried to get the title compound. Yield: 40.0 gm.

Example-7: Purification of Compound of Formula-1

A mixture of compound of formula-1 (90 gm) and dichloromethane (360 ml) was stirred for 30 min at 25-30° C. Heated the reaction mixture to 60-65° C. and stirred for 1 hr at the same temperature. Cooled the reaction mixture to 25-30° C. and stirred for 2 hrs at the same temperature. Filtered the solid, washed with dichloromethane and suck dried the material. Dichloromethane (360 ml) was added to the obtained solid at 25-30° C. and stirred the reaction mixture for 30 min at the same temperature. Heated the reaction mixture to 60-65° C. and stirred for 1 hr at the same temperature. Cooled the reaction mixture to 25-30° C. and stirred for 2 hrs at the same temperature. Filtered the solid, washed with dichloromethane and suck dried the material. Methanol (630 ml) was added to the obtained solid at 25-30° C. Heated the reaction mixture to 65-70° C. and stirred for 1 hr at the same temperature. Cooled the reaction mixture to 25-30° C. and stirred for 2 hrs at the same temperature. Filtered the solid, washed with methanol and suck dried the material. Dimethylsulfoxide (360 ml) was added to the obtained solid at 25-30° C. Heated the reaction mixture to 60-65° C. and stirred for 1 hr at the same temperature. Filtered the reaction mixture to make it particle free and washed with dimethylsulfoxide. The obtained filtrate was slowly added to pre-heated water (3600 ml) at 60-65° C. Cooled the reaction mixture to 25-30° C. and stirred for 2 hrs at the same temperature. Filtered the precipitated solid, washed with water and dried the material to get the pure title compound. Yield: 55.0 gm.

Example-8: Preparation of Compound of Formula-1

A mixture of 1-(benzo[b]thiophen-4-yl)piperazine hydrochloride (100 gm), 7-(4-chlorobutoxy)quinolin-2(1H)-one (108.6 gm), sodium iodide (29.4 gm), sodium bicarbonate (400 ml) and dimethylformamide (1000 ml) was heated to 90-95° C. and stirred for 7 hrs at the same temperature. Cooled the reaction mixture to 25-30° C., water was slowly added to it and stirred the reaction mixture for 1.5 hrs at the same temperature. Filtered the solid, washed with water and suck dried the material. Yield: 120.0 gm.

Example-9: Preparation of 7-(4-bromobutoxy)-3,4-dihydroquinolin-2(1H)-one

A mixture of 7-hydroxy-3,4-dihydroquinolin-2(1H)-one (75 gm), 1,4-dibromobutane (196.6 gm), potassium carbonate (90 gm), dimethylformamide (375 ml) and water (37.5 ml) was stirred for 19 hrs at 25-30° C. Dichloromethane was added to the reaction mixture at 25-30° C. and stirred for 30 min at the same temperature. Filtered the unwanted solid and extracted the desired compound trapper in the unwanted solid by using dichloromethane. Combined the obtained dichloromethane solution with the above obtained filtrate. Water was added to the reaction mixture at 25-30° C. and stirred for 15 min at the same temperature. Both the organic and aqueous layers were separated and extracted the aqueous layer with dichloromethane. Combined the organic layers and Washed with water. Distilled off the solvent completely from the organic layer and co-distilled with cyclohexane. Cyclohexane (75 ml) was added to the obtained compound at 25-30° C. and stirred the reaction mixture for 2 hrs at the same temperature. Filtered the solid, washed with cyclohexane and dried the material to get the title compound. Yield: 93.0 gm.

Example-10: Preparation of 7-{4-[4-(1-benzothiophen-4-yl)piperazin-1-yl]butoxy}-3,4-dihydroquinolin-2(1H)-one A mixture of 1-(benzo[b]thiophen-4-yl)piperazine hydrochloride (100 gm), 7-(4-bromobutoxy)-3,4-dihydroquinolin-2(1H)-one (128.7 gm), potassium carbonate (400 ml), sodium iodide (29.4 gm) and dimethylformamide (1000 ml) was heated to 90-95° C. and stirred for 7 hrs at the same temperature. Cooled the reaction mixture to 25-30° C., water was slowly added to it and stirred for 90 min at the same temperature. Filtered the solid, washed with water and suck dried the material. Methanol (3200 ml) and acetic acid (250 ml) were added to the obtained compound at 25-30° C. Heated the reaction mixture to 70-75° C. and stirred for 1 hr at the same temperature. Conc.HCl (60 ml) was slowly added to the reaction mixture. Cooled the reaction mixture to 5-10° C. Heated the reaction mixture to 70-75° C. and stirred for 1 hr at the same temperature. Cooled the reaction mixture to 5-10° C. and stirred for 1 hr at the same temperature. Filtered the solid, washed with methanol and suck dried the material. Water (1300 ml) and methanol (1900 ml) were added to the obtained compound at 25-30° C. Heated the reaction mixture to 80-85° C. and stirred for 1 hr at the same temperature. Charcoal (9 gm) was added to the reaction mixture and stirred for 10 min. Filtered the reaction mixture through hyflow bed and washed the hyflow bed with methanol. 25% aqueous sodium hydroxide solution was slowly added to the filtrate at 70-75° C. Water (58 ml) was added to the reaction mixture. Heated the reaction mixture to 40-45° C. and stirred for 1 hr at the same temperature. Filtered the solid, washed with methanol and dried the material to get the pure title compound. Yield: 90.0 gm.

Example-11: Preparation of Compound of Formula-1

A solution of 4,5-dichloro-3,6-dihydroxyphthalonitrile (15.52 gm) in tetrahydrofuran (100 ml) was add to a pre-cooled mixture of 7-{4-[4-(1-benzothiophen-4-yl)piperazin-1-yl]butoxy}-3,4-dihydroquinolin-2(1H)-one (25 gm) and tetrahydrofuran (50 ml) at 0-5° C. and stirred the reaction mixture for 20 min at the same temperature. Raised the temperature of the reaction mixture to 25-30° C. and stirred for 11 hrs at the same temperature. Filtered the solid, washed with tetrahydrofuran and suck dried the material. Methanol (125 ml) was added to the obtained solid at 25-30° C. Heated the reaction mixture to 50-55° C. and stirred for 1 hr at the same temperature. Cooled the reaction mixture to 25-30° C. and stirred for 1 hr at the same temperature. Filtered the solid, washed with methanol and dried the material to get the title compound. Yield: 20.0 gm.

Example-12: Purification of Compound of Formula-1

A mixture of compound of formula-1 (90 gm) and dichloromethane (360 ml) was stirred for 30 min at 25-30° C. Heated the reaction mixture to 60-65° C. and stirred for 1 hr at the same temperature. Cooled the reaction mixture to 25-30° C. and stirred for 2 hrs at the same temperature. Filtered the solid, washed with dichloromethane and suck dried the material. Dichloromethane (360 ml) was added to the obtained solid at 25-30° C. and stirred for 30 min at the same temperature. Heated the reaction mixture to 60-65° C. and stirred for 1 hr at the same temperature. Cooled the reaction mixture to 25-30° C. and stirred for 2 hrs at the same temperature. Filtered the solid, washed with dichloromethane and suck dried the material. Dimethylsulfoxide (360 ml) was added to the obtained compound at 25-30° C. Heated the reaction mixture to 60-65° C. and stirred for 1 hr at the same temperature. Filtered the reaction mixture to make it particle free and washed with dimethylsulfoxide. The obtained filtrate was slowly added to pre-heated water (3600 ml) at 60-65° C. Cooled the reaction mixture to 25-30° C. and stirred for 2 hrs at the same temperature. Filtered the solid, washed with water and dried to get the pure title compound. Yield: 70.0 gm.

Example-13: Preparation of 7-hydroxyquinolin-2(1H)-one

A solution of 4,5-dichloro-3,6-dihydroxyphthalonitrile (40.86 gm) in tetrahydrofuran (100 ml) was slowly added to a mixture of 7-hydroxy-3,4-dihydroquinolin-2(1H)-one (25 gm) and tetrahydrofuran (50 ml) at 25-30° C. and stirred the reaction mixture for 11 hrs at the same temperature. Filtered the solid, washed with tetrahydrofuran and suck dried the material. Methanol (125 ml) was added to the obtained compound at 25-30° C. Slowly heated the reaction mixture to 50-55° C. Cooled the reaction mixture to 25-30° C. and stirred for 1 hr at the same temperature. Filtered the solid, washed with methanol and dried to get the title compound. Yield: 20.3 gm; M.R: 175-180° C.

Example-14: Preparation of 7-(4-chlorobutoxy)quinolin-2(1H)-one

Potassium carbonate (60 gm) was added to a mixture of 7-hydroxyquinolin-2(1H)-one (50 gm), dimethylformamide (250 ml) and water (25 ml) at 25-30° C. and stirred the reaction mixture for 10 min at the same temperature. 1-Bromo-4-chlorobutane (95.75 gm) was added to the reaction mixture at 25-30° C. and stirred for 20 hrs at the same temperature. Water was added to the reaction mixture at 25-30° C. and stirred for 15 min at the same temperature. Methyl tert.butyl ether (200 ml) was added to the reaction mixture at 25-30° C. and stirred for 3 hrs at the same temperature. Filtered the solid and washed with water. To the obtained compound, water (250 ml) was added at 25-30° C. and stirred the reaction mixture for 40 min at the same temperature. Filtered the solid and washed with water. Methyl tert.butyl ether (150 ml) was added to the obtained compound at 25-30° C. Heated the reaction mixture to 50-55° C. and stirred for 90 min at the same temperature. Cooled the reaction mixture to 25-30° C. and stirred for 90 min at the same temperature. Filtered the solid, washed with methyl tert.butyl ether and dried the material to get the title compound. The PXRD pattern of the obtained compound is shown in FIG. 1.

Yield: 55.0 gm; M.R: 120-125° C.

Figure 2:
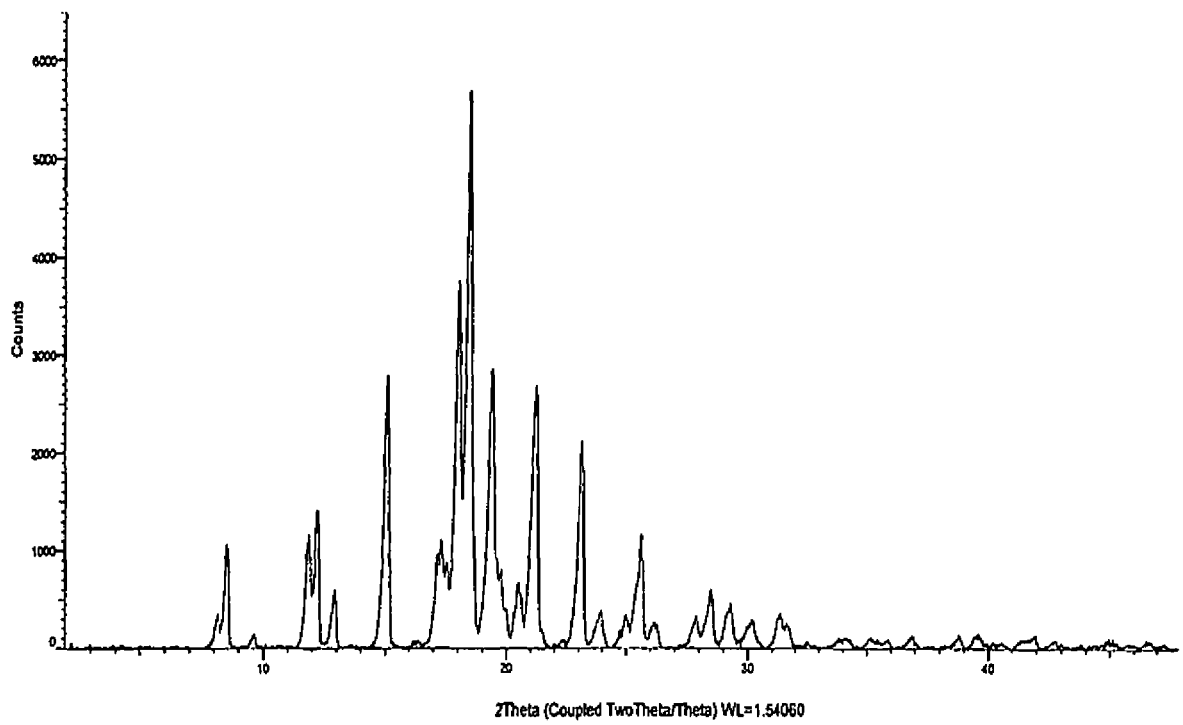

Example-15: Preparation of tert-butyl 4-(4-(2-oxo-1,2-dihydroquinolin-7-yloxy)butyl)piperazine-1-carboxylate A solution of di tert.butyl dicarbonate (67.2 gm) in methanol (300 ml) was slowly added to a solution of piperazine (53.04 gm) in methanol (300 ml) at 25-30° C. and stirred the reaction mixture for 30 min at the same temperature. Distilled off the solvent completely from the reaction mixture under reduced pressure. Water was added to the obtained compound at 25-30° C. and stirred the reaction mixture for 3 hrs at the same temperature. Filtered the reaction mixture, sodium chloride was added to the filtrate at 25-30° C. and stirred for 15 min at the same temperature. Dichloromethane was added to the reaction mixture at 25-30° C. and stirred for 15 min at the same temperature. Both the organic and aqueous layers were separated and extracted the aqueous layer with dichloromethane. Combined the organic layers and dried over sodium sulfate. Distilled off the solvent completely from the organic layer. Dimethylformamide (150 ml) was added to the obtained compound at 25-30° C. and stirred the reaction mixture for 10 min at the same temperature. 7-(4-Chlorobutoxy)quinolin-2(1H)-one (50 gm), sodium bicarbonate (21.7 gm) and sodium iodide (14.9 gm) were added to the reaction mixture at 25-30° C. Heated the reaction mixture to 90-95° C. and stirred for 7 hrs at the same temperature. Cooled the reaction mixture to 25-30° C., water was added to it and stirred for 3 hrs at the same temperature. Filtered the solid and washed with water. To the obtained solid, water (250 ml) was added at 25-30° C. and stirred the reaction mixture for 40 min at the same temperature. Filtered the solid and washed with water. Cyclohexane (300 ml) and dichloromethane (50 ml) were added to the obtained compound at 25-30° C. Heated the reaction mixture to 50-55° C. and stirred for 90 min at the same temperature. Cooled the reaction mixture to 5-10° C. and stirred for 90 min at the same temperature. Filtered the solid, washed with cyclohexane and dried the material to get the title compound. The PXRD pattern of the obtained compound is shown in FIG. 2.

Yield: 57.0 gm; M.R: 143-149° C.

Example-16: Preparation of 7-(4-(piperazin-1-yl)butoxy)quinolin-2(1H)-one

Figure 3:
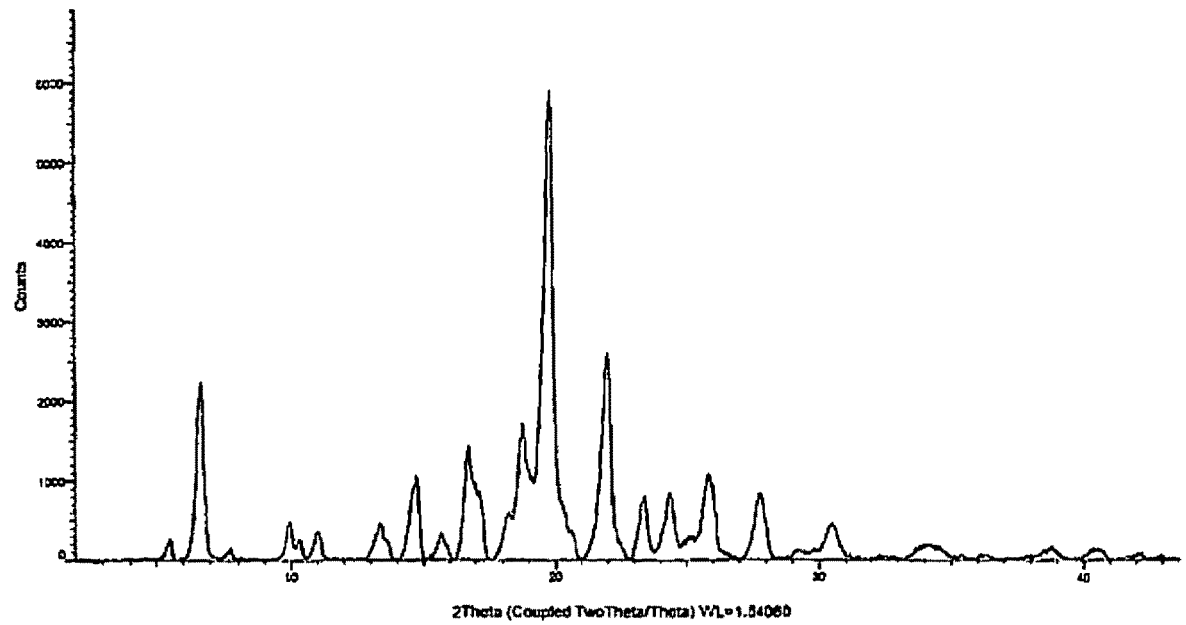
FIG. 3: Illustrates the PXRD pattern of compound of formula-7.
Figure 4:
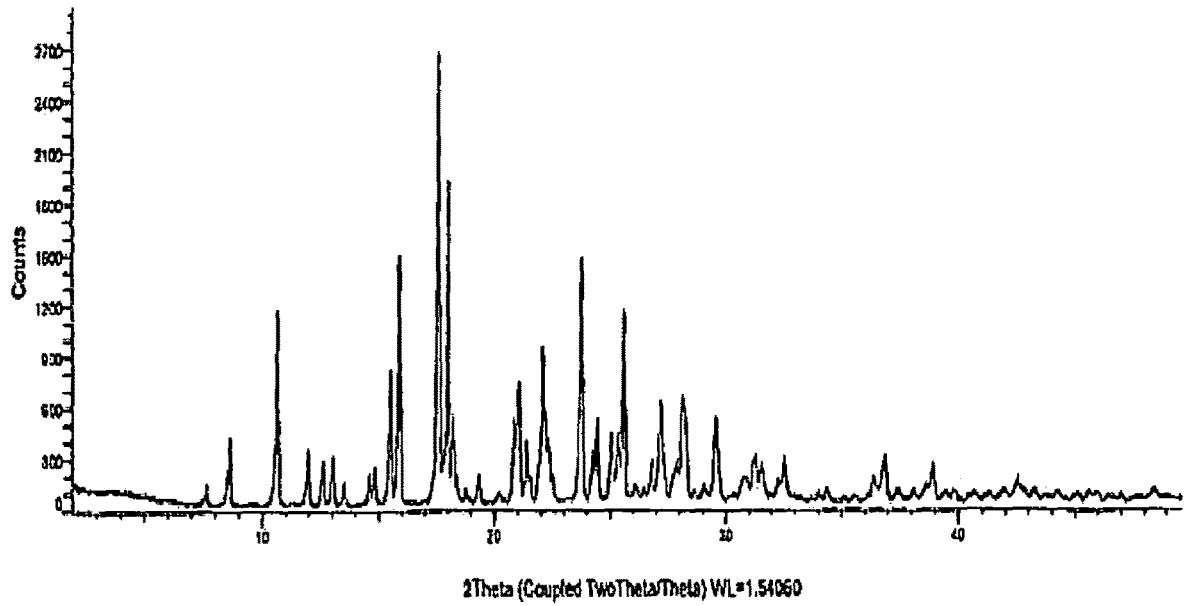

A mixture of tert-butyl 4-(4-(2-oxo-1,2-dihydroquinolin-7-yloxy)butyl)piperazine-1-carboxylate (100 gm), isopropyl alcohol (500 ml) and isopropyl alcohol-HCl (500 ml) was heated to 75-80° C. and stirred the reaction mixture for 4 hrs at the same temperature. Distilled off the solvent from the reaction mixture. Cooled the obtained compound to 25-30° C., water was added to it and stirred the reaction mixture for 1 hr at the same temperature. Filtered the reaction mixture through hyflow bed and washed the hyflow bed with water. Dichloromethane was added to the reaction mixture at 25-30° C. and stirred for 15 min at the same temperature. Both the organic and aqueous layers were separated and cooled the aqueous layer to 5-10° C. Slowly basified the reaction mixture with 10% aqueous sodium hydroxide solution at 5-10° C. and stirred the reaction mixture for 4 hrs at the same temperature. Filtered the precipitated solid, washed with acetone and suck dried the material. Methanol (250 ml) was added to the obtained compound at 25-30° C. and stirred the reaction mixture for 30 min at the same temperature. Filtered the reaction mixture through hyflow bed and washed the hyflow bed with methanol. Water (400 ml) was added to the filtrate at 25-30° C. Cooled the reaction mixture to 0-5° C. and stirred for 3 hrs at the same temperature. Filtered the precipitated solid, washed with acetone and dried the material to get the title compound. The PXRD pattern of the obtained compound is shown in FIG. 3.

Yield: 50.0 gm; M.R: 137-142° C.

Example-17: Preparation of Compound of Formula-1

7-(4-(piperazin-1-yl)butoxy)quinolin-2(1H)-one (45.96 gm), 4-bromobenzo[b] thiophene (25 gm), sodium tert.butoxide (45.1 gm), Pd(OAc)$_2$ (1.31 gm) and 1,4-dioxane (200 ml) were charged into a clean dry RBF at 25-30° C. Purged the nitrogen gas into the reaction mixture for 15 min. BINAP (1.46 gm) was added to the reaction mixture at 25-30° C. Heated the reaction mixture to 95-100° C. and stirred for 13 hrs at the same temperature. Distilled off the solvent from the reaction mixture and then cooled to 25-30° C. Water and dichloromethane were added to the reaction mixture at 25-30° C. 2N HCl solution was slowly added to the reaction mixture (dissolve 35 ml of conc.HCl in 140 ml of water) at 25-30° C. and stirred the reaction mixture for 40 min at the same temperature. Filtered the reaction mixture and both the organic and aqueous layers were separated from the filtrate. Slowly acidified the organic layer using conc.HCl (50 ml) at 25-30° C. Methanol (25 ml) was added to the reaction mixture at 25-30° C. and stirred the reaction mixture for 2 hrs at the same temperature. Filtered the solid, washed with dichloromethane and suck dried the material. Methanol (125 ml) was added to the obtained solid at 25-30° C. Conc.HCl (125 ml) was added to the reaction mixture at 25-30° C. and stirred for 1 hr at the same temperature. Filtered the solid, washed with water and suck dried the material. Methanol (250 ml), water (250 ml) and charcoal (2.5 gm) were added to the obtained compound at 25-30° C. Heated the reaction mixture to 85-90° C. and stirred for 90 min at the same temperature. Filtered the reaction mixture through hyflow bed and washed the hyflow bed with hot water. Heated the filtrate to 85-90° C. and slowly basified with aqueous sodium hydroxide solution at the same temperature. Cooled the reaction mixture to 25-30° C. and stirred for 2 hrs at the same temperature. Filtered the precipitated solid, washed with water and dried to get title compound. Yield: 30.0 gm; M.R: 183-185° C.

Example-18: Alternate Process for the Preparation of Compound of Formula-1

A mixture of 4-bromobenzo[b]thiophene (50 gm), Pd(OAc)$_2$ (1.05 gm) and 1,4-dioxane (400 ml) was stirred for 10 min at 25-30° C. under N$_2$ atmosphere. 7-(4-(piperazin-1-yl)butoxy)quinolin-2(1H)-one (127.3 gm) and sodium tert.butoxide (90.2 gm) were added to the reaction mixture at 25-30° C. and stirred for 10 min at the same temperature. Purged the nitrogen gas into the reaction mixture for 15 min. BINAP (5.84 gm) was added to the reaction mixture under nitrogen atmosphere at 25-30° C. Heated the reaction mixture to 95-100° C. and stirred for 7 hrs at the same temperature. Reduced the temperature of the reaction mixture to 60-65° C., ethyl acetate was added to it and stirred the reaction mixture for 40 min at the same temperature. Water was added to the reaction mixture at 60-65° C.

and stirred for 10 min at the same temperature. Cooled the reaction mixture to 25-30° C. and filtered through hyflow bed and washed the hyflow bed with ethyl acetate. Both the organic and aqueous layers were separated from the filtrate. Distilled off the solvent completely from the organic layer and co-distilled with methanol. Cooled the reaction mixture to 25-30° C., methanol (250 ml) followed by conc.HCl (150 ml) were added to the obtained compound. Heated the reaction mixture to 65-70° C. and stirred for 3 hrs at the same temperature. Cooled the reaction mixture to 25-30° C. and stirred for 2 hrs at the same temperature. Filtered the solid and washed with methanol. Methanol (350 ml) was added to the obtained compound at 25-30° C. Heated the reaction mixture to 60-65° C. and stirred for 2 hrs at the same temperature. Cooled the reaction mixture to 5-10° C. and stirred for 1 hr at the same temperature. Filtered the solid and washed with methanol. Dichloromethane (350 ml) was added to the obtained compound at 25-30° C. and stirred the reaction mixture for 1 hr at the same temperature. Filtered the solid and washed with dichloromethane. Methanol (900 ml) was added to the obtained compound at 25-30° C. Heated the reaction mixture to 75-80° C. and water (600 ml) was slowly added to it at the same temperature. Charcoal (5 gm) was added to the reaction mixture at 75-80° C. and stirred for 30 min at the same temperature. Filtered the reaction mixture through hyflow bed and washed the hyflow bed with methanol. Cooled the filtrate to 25-30° C., aqueous ammonia solution (400 ml) was slowly added to it and stirred the reaction mixture for 20 min at the same temperature. Heated the reaction mixture to 60-65° C. and stirred for 90 min at the same temperature. Cooled the reaction mixture to 25-30° C., dichloromethane was added to it and stirred the reaction mixture for 30 min at the same temperature. Both the organic and aqueous layers were separated. Distilled off the solvent completely from the organic layer and co-distilled with methanol. Cooled the reaction mixture to 25-30° C., methanol (100 ml) was added to it. Heated the reaction mixture to 60-65° C. and stirred for 1 hr at the same temperature. Cooled the reaction mixture to 25-30° C. and stirred for 2 hrs at the same temperature. Filtered the solid, washed with methanol and dried to get the title compound. Yield: 61.0 gm.

Example-19: Purification of Compound of Formula-1

A mixture of compound of formula-1 (25 gm) and dimethylsulfoxide (175 ml) was stirred for 30 min at 25-30° C. Heated the reaction mixture to 60-65° C. and stirred for 40 min at the same temperature. Charcoal (2.5 gm) was added to the reaction mixture at 60-65° C. and stirred for 40 min at the same temperature. Filtered the reaction mixture to make it particle free and washed with dimethylsulfoxide. The obtained filtrate was slowly added to pre-heated water (550 ml) at 60-65° C. Cooled the reaction mixture to 25-30° C. and stirred for 3 hrs at the same temperature. Filtered the precipitated solid, washed with water and dried the material to get the pure title compound. Yield: 20.0 gm; M.R: 183.5-184.5° C. The PXRD pattern of the obtained compound is similar to PXRD of anhydrous crystalline form-I of Brexpiprazole disclosed in WO2013/162046 A1.

Example-20: Preparation of 7-hydroxyquinolin-2(1H)-one

A mixture of 7-hydroxy-3,4-dihydroquinolin-2(1H)-one (20 Kg) and tetrahydrofuran (40 Lt) was stirred for. 10 min at 25-30° C. A solution of 4,5-dichloro-3,6-dihydroxyphthalonitrile (33.4 Kg) in tetrahydrofuran (80 Lt) was slowly added to the reaction mixture at 25-30° C. and stirred for 16 hrs at the same temperature. Filtered the solid, washed with tetrahydrofuran and spin dried the material. Methanol (100 Lt) was added to the obtained compound at 25-30° C. Heated the reaction mixture to 50-55° C. and stirred for 1 hr at the same temperature. Cooled the reaction mixture to 25-30° C. and stirred for 1 hr at the same temperature. Filtered the solid, washed with methanol and dried the material to get the title compound. Yield: 17.3 Kg; Purity by UPLC: 98.25%.

Example-21: Preparation of 7-(4-chlorobutoxy)quinolin-2(1H)-one

A mixture of 7-hydroxyquinolin-2(1H)-one (17 Kg), dimethylformamide (85 Lt), water (8.5 Lt) and potassium carbonate (20.4 Kg) was stirred for 15 min at 25-30° C. 1-bromo-4-chlorobutane (32.47 Kg) was added to the reaction mixture at 25-30° C. and stirred for 20 hrs at the same temperature. Water (255 Lt) was added to the reaction mixture and stirred for 15 min. Methyl tert-butyl ether (68 Lt) was added to the reaction mixture at 25-30° C. and stirred for 3 hrs at the same temperature. Filtered the solid, washed with water and spin dried the material. Water (85 Lt) was added to the obtained compound at 25-30° C. and stirred the reaction mixture for 40 min at the same temperature. Filtered the solid, washed with water and spin dried the material. Methyl tert-butyl ether (51 Lt) was added to the obtained compound at 25-30° C. Heated the reaction mixture to 50-55° C. and stirred for 90 min at the same temperature. Cooled the reaction mixture to 25-30° C. Filtered the solid, washed with methyl tert-butyl ether and dried the material to get the title compound.
Yield: 18.8 Kg; Purity by HPLC: 93%.

Example-22: Preparation of tert-butyl 4-(4-(2-oxo-1,2-dihydroquinolin-7-yloxy)butyl)piperazine-1-carboxylate A solution of di-tert-butyl dicarbonate (24.19 Kg) in methanol (108 Lt) was slowly added to a mixture of piperazine (19.08 Kg) and methanol (108 Lt) at 25-30° C. and stirred the reaction mixture for 30 min at the same temperature. Distilled off the solvent completely from the reaction mixture under reduced pressure. Water (234 Lt) was added to the reaction mixture at 25-30° C. and stirred for 3 hrs at the same temperature. Filtered the reaction mixture through hyflow bed and washed the hyflow bed with water. Sodium chloride followed by dichloromethane were added to the reaction mixture at 25-30° C. and stirred for 15 min at the same temperature. Both the organic and aqueous layers were separated and extracted the aqueous layer with dichloromethane. Combined the organic layers and dried over sodium sulfate. Distilled off the solvent completely from the organic layer under reduced pressure. Dimethylformamide (54 Lt) was added to the obtained compound at 25-30° C. and stirred the reaction mixture for 15 min at the same temperature. 7-(4-Chlorobutoxy)quinolin-2(1H)-one (18 Kg), sodium bicarbonate (7.81 Kg) and sodium iodide (5.4 Kg) were added to the reaction mixture at 25-30° C. and stirred for 10 min at the same temperature. Heated the reaction mixture to 90-95° C. and stirred for 6 hrs at the same temperature. Cooled the reaction mixture to 25-30° C., water (180 Lt) was slowly added to it and stirred for 3 hrs at the same temperature. Filtered the solid, washed with water and spin dried the material. Water (90 Lt) was added to the obtained compound at 25-30° C. and stirred the reaction mixture for 40 min at the same temperature. Filtered the solid, washed with water and spin dried the material. Cyclohexane (108 Lt) and dichloromethane (27 Lt) were added to the obtained compound at 25-30° C. Heated the reaction mixture to 50-55° C. and stirred for 90 min at the same temperature. Cooled the reaction mixture to 5-10° C. and stirred for 90 min at the same temperature. Filtered the solid, washed with cyclohexane and dried the material to get the title compound. Yield: 23.5 Kg; Purity by HPLC: 95.5%.

Example-23: Preparation of 7-(4-(piperazin-1-yl)butoxy)quinolin-2(1H)-one

A mixture of tert-butyl 4-(4-(2-oxo-1,2-dihydroquinolin-7-yloxy)butyl)piperazine-1-carboxylate (23 Kg), isopropyl alcohol (115 Lt) and isopropyl alcohol-HCl (115 Lt) was heated to 75-80° C. and stirred the reaction mixture for 4 hrs at the same temperature. Distilled off the solvent completely from the reaction mixture under reduced pressure. Cooled the reaction mixture to 25-30° C., water (161 Lt) was added to it and stirred for 1 hr at the same temperature. Filtered the reaction mixture through hyflow bed and washed the hyflow bed with water. Dichloromethane was added to the filtrate at 25-30° C. and stirred the reaction mixture for 20 min at the same temperature. Both the organic and aqueous layers were separated and cooled the aqueous layer to 5-10° C. Slowly basified the aqueous layer by using aqueous sodium hydroxide solution at 5-10° C. and stirred the reaction mixture for 4 hrs at the same temperature. Filtered the solid, washed with cold acetone and spin dried the material. Methanol (57.5 Lt) was added to the obtained compound at 25-30° C. and stirred the reaction mixture for 30 min at the same temperature. Filtered the reaction mixture through hyflow bed and washed with methanol. Water (92 Lt) was added to the filtrate at 25-30° C., cooled the reaction mixture to 0-5° C. and stirred for 3 hrs at the same temperature. Filtered the solid, washed with cold acetone and dried the material to get the title compound.
Yield: 10.6 Kg; Water content by KFR: 0.47% w/w; Purity by HPLC: 98.8%.

Example-24: Preparation of Compound of Formula-1

A mixture of 1,4-dioxane (32 Lt), palladium acetate (0.084 Kg) and 4-bromobenzo[b]thiophene (4 Kg) was stirred for 10 min at 25-30° C. 7-(4-(piperazin-1-yl)butoxy)quinolin-2(1H)-one (10.2 Kg) and sodium tert.butoxide (7.2 Kg) were added to the reaction mixture at 25-30° C. and stirred for 10 min at the same temperature. Nitrogen gas was purged into the reaction mixture and 2,2'-bis(diphenylphosphino)-1,1'-binaphthyl (0.468 Kg) was added to it at 25-30° C. Heated the reaction mixture to 95-100° C. and stirred for 7 hrs at the same temperature. Cooled the reaction mixture to 60-65° C., ethyl acetate (80 Lt) was added to it and stirred for 40 min at the same temperature. Water (72 Lt) was added to the reaction mixture at 60-65° C. and stirred for 10 min at the same temperature. Further cooled the reaction mixture to 25-30° C., filtered it through hyflow bed and washed with ethyl acetate. Both the organic and aqueous layers were separated from the filtrate and extracted the aqueous layer with ethyl acetate. Combined the organic layers, distilled off the solvent completely from the organic layer under reduced pressure and co-distilled with methanol. Methanol (20 Lt) followed by hydrochloric acid (12 Lt) were added to the obtained compound at 25-30° C. Heated the reaction mixture to 65-70° C. and stirred for 3 hrs at the same temperature. Cooled the reaction mixture to 25-30° C. and stirred for 2 hrs at the same temperature. Filtered the solid, washed with methanol and spin dried the material. Methanol (20 Lt) and hydrochloric acid (12 Lt) were added to the obtained compound at 25-30° C. Heated the reaction mixture to 65-70° C. and stirred for 3 hrs at the same temperature. Cooled the reaction mixture to 25-30° C. and stirred for 2 hrs at the same temperature. Filtered the solid, washed with methanol and spin dried the material. Methanol (28 Lt) was added to the obtained compound at 25-30° C. Heated the reaction mixture to 60-65° C. and stirred for 2 hrs at the same temperature. Cooled the reaction mixture to 5-10° C. and stirred for 1 hr at the same temperature. Filtered the solid, washed with methanol and spin dried the material. Dichloromethane (28 Lt) was added to the obtained compound at 25-30° C. and stirred the reaction mixture for 1 hr at the same temperature. Filtered the solid, washed with dichloromethane and spin dried the material. Methanol (152 Lt) was added to the obtained compound at 25-30° C. Heated the reaction mixture to 60-65° C. and water (96 Lt) was slowly added to it. Heated the reaction mixture to 75-80° C., activated charcoal (0.4 Kg) was added to it and stirred for 30 min at the same temperature. Filtered the reaction mixture through hyflow bed and washed the material with methanol. Cooled the filtrate to 25-30° C., basified it with aq. ammonia solution (32 Lt) and stirred for 20 min at the same temperature. Heated the reaction mixture to 60-65° C. and stirred for 90 min at the same temperature. Cooled the reaction mixture to 25-30° C., dichloromethane was added to it and stirred for 30 min at the same temperature. Both the organic and aqueous layers were separated, distilled off the solvent completely from the organic layer and co-distilled with methanol. Methanol (12 Lt) was added to the obtained compound at 25-30° C. Heated the reaction mixture to 60-65° C. and stirred for 1 hr at the same temperature. Cooled the reaction mixture to 25-30° C. and stirred for 2 hrs at the same temperature. Filtered the solid, washed with methanol and dried to get title compound.
Yield: 4.4 Kg; Water content by KFR: 0.27% w/w; Purity by HPLC: 99.7%.

Example-25: Purification of Compound of Formula-1

A mixture of compound of formula-1 (4 Kg) and dimethyl sulfoxide (30 Lt) was stirred for 10 min at 25-30° C. Heated the reaction mixture to 60-65° C. and stirred for 40 min at the same temperature. The reaction mixture was slowly added to pre-heated water (88 Lt) at 60-65° C. Cooled the reaction mixture to 25-30° C. and stirred for 3 hrs at the same temperature. Filtered the solid, washed with water and dried the material to get the title compound. Yield: 3.21 Kg; Water content by KFR: 0.44% w/w; Purity by HPLC: 99.72%. Piperazine quinoline impurity: 0.05%; Piperazine butoxy dimer impurity: 0.01%; Bromo benzothiophene impurity: Not detected; The PXRD pattern of the obtained compound is similar to PXRD of anhydrous crystalline form-I of Brexpiprazole disclosed in WO2013/162046 A1.
Particle Size Distribution:
Before micronization: D(0.1) is 0.94 µm; D(0.5) is 3.99 µm; D(0.9) is 8.04 µm.
After micronization: D(0.1) is 0.37 µm; D(0.5) is 2.04 µm; D(0.9) is 4.47 µm.

Example-26: Preparation of 7-hydroxyquinolin-2(1H)-one 4,5-Dichloro-3,6-dihydroxyphthalonitrile (40.86 gm) was slowly added to a mixture of 7-hydroxy-3,4-dihydroquinolin-2(1H)-one (25 gm) and 1,4-dioxane (250 ml) at 25-30° C. Heated the reaction mixture to 80-85° C. and stirred for 7 hrs at the same temperature. Cooled the reaction mixture to 25-30° C. Filtered the solid, washed with 1,4-dioxane and suck dried the material. The obtained compound was added to methanol (125 ml) at 25-30° C. Heated the reaction mixture to 50-55° C. Cooled the reaction mixture to 25-30° C. and stirred for 1 hr at the same temperature. Filtered the solid, washed with methanol and dried the material to get the title compound. Yield: 20.3 gm; M.R.: 175-180° C.

Example-27: Preparation of ethyl 4-(2-oxo-1,2-dihydroquinolin-7-yloxy)butanoate A mixture of 7-hydroxyquinolin-2(1H)-one (50 gm), dimethyl formamide (1000 ml) and potassium carbonate (85 gm) was stirred for 1 hr at 25-30° C. Ethyl 4-bromobutanoate (90.7 gm) was slowly added to the reaction mixture at 25-30° C. and stirred the reaction mixture for 10 hrs at the same temperature. Water and dichloromethane were added to the reaction mixture at 25-30° C. and stirred for 10 min at the same temperature. Both the organic and aqueous layers were separated and extracted the aqueous layer with dichloromethane. Combined the organic layers and washed with water. Distilled off the solvent completely from the organic layer. Methyl tert.butyl ether (250 ml) was added to the obtained compound at 25-30° C. and stirred the reaction mixture for 3 hrs at the same temperature. Filtered the solid, washed with methyl tert.butyl ether and dried the material to get the title compound.
Yield: 53.0 gm.

Example-28: Preparation of 4-(2-oxo-1,2-dihydroquinolin-7-yloxy)butanoic acid Lithium hydroxide hydrate (3.05 gm) was added to a mixture of ethyl 4-(2-oxo-1,2-dihydroquinolin-7-yloxy)butanoate (10 gm), isopropyl alcohol (50 ml) and water (50 ml) at 25-30° C. and stirred the reaction mixture for 7 hrs at the same temperature. Ethyl acetate was added to the reaction mixture at 25-30° C. and stirred for 10 min at the same temperature. Both the organic and aqueous layers were separated. Acidified the aqueous layer with 2N aqueous HCl solution at 25-30° C. and stirred the reaction mixture for 3 hrs at the same temperature. Filtered the precipitated solid, washed with water and dried the material to get the title compound.
Yield: 6.3 gm.

Example-29: Preparation of 1-(benzo[b]thiophen-4-yl)piperazine

10% Aqueous potassium carbonate solution (50 gm of potassium carbonate in 250 ml of water) was slowly added to a mixture of 1-(benzo[b]thiophen-4-yl)piperazine hydrochloride (50 gm), dichloromethane (500 ml) and water (500 ml) at 25-30° C. and stirred the reaction mixture for 1 hr at the same temperature. Both the organic and aqueous layers were separated and extracted the aqueous layer with dichloromethane. Combined the organic layers and distilled off the solvent completely to get the title compound.
Yield: 42.0 gm.

Example-30: Preparation of 7-(4-(4-(benzo[b]thiophen-4-yl)piperazin-1-yl)-4-oxobutoxy)quinolin-2(1H)-one A mixture of 4-(2-oxo-1,2-dihydroquinolin-7-yloxy)butanoic acid (5 gm), dichloromethane (75 ml) and dimethylformamide (0.25 ml) was stirred for 10 min at 25-30° C. Thionyl chloride (3.63 ml) was slowly added to the reaction mixture at 25-30° C. and stirred for 3 hrs at the same temperature. Distilled the reaction mixture and co-distilled with dichloromethane. Dichloromethane (50 ml) was added to the reaction mixture at 25-30° C. and stirred for 10 min at the same temperature. 1-(benzo[b]thiophen-4-yl)piperazine (5.3 gm) and dichloromethane (50 ml) were added to the reaction mixture at 25-30° C. Cooled the reaction mixture to 0-5° C. and triethylamine (5.67 ml) was slowly added to it at the same temperature. Raised the temperature of the reaction mixture to 25-30° C. and stirred for 16 hrs at the same temperature. Dichloromethane was added to the reaction mixture at 25-30° C. and stirred for 1 hr at the same temperature. Filtered the reaction mixture and distilled off the solvent from the filtrate. The obtained compound was purified by column chromatography by using cyclohexane/ethyl acetate as eluent. Distilled off the solvent completely from the wanted fractions under reduced pressure and dried the solid to provide the title compound.
Yield: 2.3 gm.

Example-31: Preparation of Compound of Formula-1

Borane-dimethylsulfide (8.47 ml) was added to a precooled mixture of 7-(4-(4-(benzo[b]thiophen-4-yl)piperazin-1-yl)-4-oxobutoxy)quinolin-2(1H)-one (20 gm) and tetrahydrofuran (140 ml) at 0-5° C. Raised the temperature of the reaction mixture to 25-30° C. and stirred for 16 hrs at the same temperature. Cooled the reaction mixture to 0-5° C. and slowly quenched the reaction mixture with 2N aqueous HCl solution. Dichloromethane was added to the reaction mixture at 0-5° C. Raised the temperature of the reaction mixture to 25-30° C. and stirred for 2 hrs at the same temperature. Filtered the solid, washed with dichloromethane and dried the material to get the title compound. Yield: 6.0 gm.

Example-32: Purification of Compound of Formula-1

A mixture of compound of formula-1 (6 gm), dichloromethane (60 ml) and 2N HCl solution (6 ml of conc.HCl in 24 ml of water) was heated to 40-45° C. and stirred for 1 hr at the same temperature. Cooled the reaction mixture to 25-30° C. and stirred for 1 hr at the same temperature. Filtered the solid and washed with dichloromethane. Dichloromethane and water were added to the obtained compound at 25-30° C. Aqueous ammonia solution (30 ml) was slowly added to the reaction mixture at 25-30° C. and stirred for 40 min at the same temperature. Both the organic and aqueous layers were separated and extracted the aqueous layer with dichloromethane. Combined the organic layers and distilled off the solvent completely and co-distilled with methanol. Methanol (30 ml) was added to the obtained compound at 25-30° C. Heated the reaction mixture to 60-65° C. and stirred for 1 hr at the same temperature. Cooled the reaction mixture to 25-30° C. and stirred for 1 hr at the same temperature. Filtered the solid, washed with methanol and dried the material to get the title compound. Yield: 1.5 gm.

We claim:

1. A process for the purification of 7-{4-[4-(1-benzothiophen-4-yl)piperazin-1-yl]butoxy}quinolin-2(1H)-one compound of formula-1,

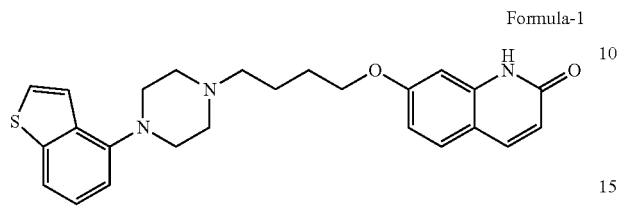

Formula-1 comprising:
a) providing a solution of compound of formula-1 in a solvent selected from the group consisting of polar-aprotic solvents, alcohol solvents, chloro solvents, and a mixture thereof,
b) optionally treating the reaction mixture with charcoal,
c) combining the solution with an anti-solvent selected from the group consisting of polar solvents, hydrocarbon solvents, ether solvents, ester solvents, ketone solvents, nitrile solvents, and a mixture thereof, and optionally cooling the reaction mixture to provide pure compound of formula-1.

2. The process according to claim 1, wherein, combining the solution of step-a) or step-b) with the anti-solvent can be carried out at a temperature ranging from 0° C. to 100° C.; and the reaction mixture in step-c) can be optionally cooled to a temperature ranging from −25° C. to 25° C.

3. The process according to claim 2, wherein the solvent is a polar-aprotic solvent and the anti-solvent is a polar solvent.

4. The process according to claim 3, wherein the solvent is dimethyl sulfoxide and the anti-solvent is water.

* * * * *